(12) United States Patent
Poe et al.

(10) Patent No.: US 10,765,693 B2
(45) Date of Patent: Sep. 8, 2020

(54) POLYMORPHIC COMPOUNDS AND USES THEREOF

(71) Applicant: Astrocyte Pharmaceuticals, Inc., Cambridge, MA (US)

(72) Inventors: Russell Birch Poe, Groton Long Point, CT (US); David T. Jonaitis, Brookston, IN (US); Lisa Michelle Grove, Lafayette, IN (US)

(73) Assignee: Astrocyte Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 16/583,570

(22) Filed: Sep. 26, 2019

(65) Prior Publication Data

US 2020/0093848 A1     Mar. 26, 2020

Related U.S. Application Data

(60) Provisional application No. 62/736,979, filed on Sep. 26, 2018.

(51) Int. Cl.
*A61K 31/7076* (2006.01)
*C07H 19/16* (2006.01)

(52) U.S. Cl.
CPC ......... *A61K 31/7076* (2013.01); *C07H 19/16* (2013.01); *C07B 2200/13* (2013.01)

(58) Field of Classification Search
CPC .......................... A61K 31/7076; C07H 19/16
See application file for complete search history.

(56) References Cited

U.S. PATENT DOCUMENTS

| | | | |
|---|---|---|---|
| 5,773,423 A | 6/1998 | Jacobson et al. | |
| 6,586,413 B2 | 7/2003 | Liang et al. | |
| 7,064,112 B1 | 6/2006 | Fishman | |
| 7,087,589 B2 | 8/2006 | Jacobson et al. | |
| 7,348,315 B2 | 3/2008 | Liang et al. | |
| 7,414,036 B2 | 8/2008 | Sevillano et al. | |
| 7,589,075 B2 | 9/2009 | Fishman et al. | |
| 7,790,735 B2 | 9/2010 | Jacobson et al. | |
| 7,825,126 B2 | 11/2010 | Jacobson et al. | |
| 7,867,983 B2 | 1/2011 | Liang et al. | |
| 8,399,018 B2 | 3/2013 | Lichter et al. | |
| 8,410,078 B2 | 4/2013 | Liang et al. | |
| 8,518,957 B2 | 8/2013 | Jacobson et al. | |
| 8,685,372 B2 | 4/2014 | Tsien et al. | |
| 8,691,775 B2 | 4/2014 | Wurtman | |
| 8,735,407 B2 | 5/2014 | Jacobson et al. | |
| 8,796,291 B2 | 8/2014 | Jacobson et al. | |
| 8,822,434 B2 | 9/2014 | Liang et al. | |
| 8,916,570 B2 | 12/2014 | Jacobson et al. | |
| 9,132,131 B2 | 9/2015 | Salvemini | |
| 9,181,253 B2 | 11/2015 | Jacobson et al. | |
| 9,387,220 B2 | 7/2016 | Fishman et al. | |
| 9,526,739 B2 | 12/2016 | Liang et al. | |
| 9,789,131 B1 | 10/2017 | Korinek et al. | |
| 9,963,450 B2 | 5/2018 | Jacobson et al. | |
| 10,265,338 B2 | 4/2019 | Korinek et al. | |
| 2003/0216412 A1* | 11/2003 | Jacobson ............. | C07D 473/34 514/263.4 |
| 2009/0306225 A1 | 12/2009 | Lichter et al. | |
| 2010/0256086 A1 | 10/2010 | Fischer | |
| 2014/0241990 A1 | 8/2014 | Haydon et al. | |
| 2018/0021363 A1 | 1/2018 | Korinek et al. | |

FOREIGN PATENT DOCUMENTS

| | | |
|---|---|---|
| EP | 1624753 B1 | 1/2012 |
| WO | WO-2006031505 A1 | 3/2006 |
| WO | WO-2006091905 A1 | 8/2006 |
| WO | WO-2007020018 A1 | 2/2007 |
| WO | WO-2008021552 A2 | 2/2008 |
| WO | WO-2010014921 A2 | 2/2010 |
| WO | WO-2011077435 A1 | 6/2011 |
| WO | WO-2014160502 A1 | 10/2014 |
| WO | WO-2016123672 A1 | 8/2016 |
| WO | WO-2017/185061 A1 | 10/2017 |
| WO | WO-2019157317 A1 | 8/2019 |

OTHER PUBLICATIONS

Mane et al., Neuropharmacology, 2016, 110, p. 376-385. (Year: 2016).*
Vippagunta et al., Advanced Drug Delivery Reviews, 2001, 48, p. 3-26. (Year: 2001).*
Brittain, H.G., ed., Polymorphism in Pharmaceutical Solids, 1999, Marcel Dekker Inc., p. 183-226. (Year: 1999).*
Ando et al., "A comparative analysis of the activity of ligands acting at P2X and P2Y receptor subtypes in models of neuropathic, acute and inflammatory pain," British Journal of Pharmacology, vol. 159, No. 5, Mar. 2010 (pp. 1106-1117).
Armstrong et al., "Adenosine receptor specificity in preconditioning of isolated rabbit cardiomyocytes: evidence of $A_3$ receptor involvement," Cardiovascular Research, vol. 28, No. 7, Jul. 1994 (pp. 1049-1056).
Auchampach et al., "Selective Activation of $A_3$ Adenosine Receptors with $N^6$-(3-Iodobenzyl)Adenosine-5'-N-Methyluronamide Protects Against Myocardial Stunning and Infarction without Hemodynamic Changes in Conscious Rabbits," Circulation Research, vol. 80, Jun. 1997 (pp. 800-809).
Baltos et al., "Structure-Activity Analysis of Biased Agonism at the Human Adenosine $A_3$ Receptor," Molecular Pharmacology, vol. 90, No. 1, Jul. 2016 (pp. 12-22).
Barragán-Iglesias et al., "Participation of Peripheral $P2Y_1$, $P2Y_6$ and $P2Y_{11}$ receptors in formalin-induced inflammatory pain in rats," Pharmacology, Biochemistry and Behavior, vol. 128, Jan. 2015 (pp. 23-32).

(Continued)

*Primary Examiner* — Jonathan S Lau
(74) *Attorney, Agent, or Firm* — Andrea L. C. Reid; Joseph W. Arico; Dechert LLP

(57) ABSTRACT

The present invention provides compounds and methods of use thereof for treatment of certain disorders and conditions, for example brain injuries such as stroke or traumatic brain injuries.

13 Claims, 18 Drawing Sheets

(56) References Cited

OTHER PUBLICATIONS

Ben et al., "Different efficacy of adenosine and NECA derivatives at the human $A_3$ adenosine receptor: insight into the receptor activation switch," Biochemical Pharmacology, vol. 87, No. 2, Jan. 2014 (pp. 321-331).

Beukers et al., "New, non-adenosine, high-potency agonists for the human adenosine A2B receptor with an improved selectivity profile compared to the reference agonist N-ethylcarboxamidoadenosine," Journal of Medicinal Chemistry, vol. 47, No. 15, Jul. 2004 (pp. 3707-3709).

Björklund et al., "Adenosine $A_1$ and $A_3$ receptors protect astrocytes from hypoxic damage," European Journal of Pharmacology, vol. 596, No Month Listed 2008 (pp. 6-13).

Borea et al., "The $A_3$ Adenosine Receptor: History and Perspectives," Pharmacological Reviews, vo. 67, Jan. 2015 (pp. 74-102).

Bourdon et al., "(N)-methanocarba-2MeSADP (MRS2365) is a subtype-specific agonist that induces rapid desensitization of the $P2Y_1$, receptor of human platelets," Journal of Thrombosis and Haemostasis, vol. 4, No. 4, Apr. 2006 (pp. 861-868).

Camaioni et al., "Adenosine receptor agonists: synthesis and biological evaluation of the disatereoisomers of 2-(3-hydroxy-3-phenyl-1-propyn-1-yl)NECA," Bioorganic & Medicinal Chemistry, vol. 5, No. 12, Dec. 1997 (pp. 2267-2275).

Chen et al., "Activation of Adenosine A3 Receptors Reduces Ischemic Brain Injury in Rodents," Journal of Neuroscience Research, vol. 84, No Month Listed 2006 (pp. 1848-1855).

Choi et al., "A3 Adenosine Receptor Agonist Reduces Brain Ischemic Injury and Inhibits Inflammatory Cell Migration in Rats," The America Journal of Pathology, vol.179, No. 4, Oct. 2011 (pp. 2042-2052).

Ciancetta et al., "Structural Probing and Molecular Modeling of the $A_3$ Adenosine Receptor: A Focus on Agonist Binding," Molecules, vol. 22, No. 3, Mar. 2017 (17 pages).

Cosyn et al., "2-Triazole-Substituted Adenosines: A New Class of Selective $A_3$ Adenosine Receptor Agonists, Partial Agonists, and Antagonists," The Journal of Medicinal Chemistry, vol. 49, No. 25, Dec. 2006 (pp. 7373-7383).

Cosyn et al., "Synthesis of hypermodified adenosine derivatives as selective adenosine $A_3$ receptor ligands," Bioorganic & Medicinal Chemistry, vol. 14, 2006 (pp. 1403-1412) (Nov. 2005).

Cristalli et al., "2-Aralkynyl and 2-Heteroalkynyl derivatives of adenosine-5'-N-ethyluronamide as selective A2a adenosine receptor agonists," Journal of Medicinal Chemistry, vol. 38, No. 9, Apr. 1995 (pp. 1462-1472).

D'Alimonte et al., "Potentiation of temozolomide antitumor effect by purine receptor ligands able to restrain the in vitro growth of human glioblastoma stem cells," Purinergic Signalling, vol. 11, No. 3, Sep. 2015 (pp. 331-346).

Devine et al., "Synthesis and evaluation of new $N^6$-substituted adenosine-5'-N-methylcaiboxamides as $A_3$ adenosine receptor agonists," Bioorganic & Medicinal Chemistry, vol. 18, No. 8, May 2010 (pp. 3078-3087).

Doyle et al., "Adenosine $A_3$ Receptor Expression and Function in Mitochondria," The FASEB Journal, vol. 30, No. 1, Apr. 2016, Supplement 1266.6 (2 pages).

Fedorova et al., "Behavioral Characterization of Mice Lacking the $A_3$ Adenosine Receptor: Sensitivity to Hypoxic Neurodegeneration," Cell Molecular Neurobiology, vol. 23, No. 3, Jun. 2003 (pp. 431-447).

Gao et al., "Allosteric modulation and functional selectivity of G protein-coupled receptors," Drug Discovery Today. Technologies, vol. 10, No. 2, No Month Listed 2013 (pp. e237-e243).

Gao et al., "Functionally biased modulation of $A_3$ adenosine receptor agonist efficacy and potency by imidazoquinolinamine allosteric enhancers," Biochemical Pharmacology, vol. 82, No. 6, Sep. 2011 (pp. 658-668).

Gao et al., "Partial Agonists for $A_3$ Adenosine Receptors," Current Topics in Medicinal Chemistry, vol. 4, No. 8, Apr. 2004 (pp. 855-862).

Gao et al., "Structural Determinants of $A_3$ Adenosine Receptor Activation: Nucleoside Ligands at the Agonist/Antagonist boundary," Journal of Medicinal Chemistry, vol. 45, No. 20, Aug. 2002 (pp. 4471-4484).

Goadsby et al., "Adenosine A1 receptor agonists inhibit trigeminovascular nociceptive transmission," Guarantors of Brain, 2002 (pp. 1392-1401).

Gundry et al., "A Practical Guide to Approaching Biased Agonism at G Protein Coupled Receptors," Frontiers in Neuroscience, vol. 11, No. 17, Jan. 2017 (6 pages).

International Search Report and Written Opinion issued in PCT/US2017/028996 dated Aug. 2, 2017 (10 pages).

Jacobson et al., "Medicinal Chemistry of the $A_3$ Adenosine Receptor: Agonists, Antagonists, and Receptor Engineering," Handbook Experimental Pharmacology, vol. 193, No Month Listed 2009 (pp. 123-159).

Jacobson et al., "P2Y nucleotide receptors: Promise of therapeutic applications," Drug Discovery Today, vol. 15, Nos. 13-14, Jul. 2010 (pp. 570-578).

Jacobson et al., "John Daly Lecture: Structure-guided Drug Design for Adenosine and P2Y Receptors," Computational and Structural Biotechnology Journal, vol. 13, Oct. 2014 (pp. 286-298).

Kim et al., "Three-dimensional quantitative structure-activity relationship of nucleosides acting at the $A_3$ adenosine receptor: analysis of binding and relative efficacy," Journal of Chemical Information and Modeling, vol. 47, No. 3, May 2007 (pp. 1225-1233).

Klotz et al., "2-substituted N-ethylcarboxamidoadenosine derivatives as high-affinity agonists as human $A_3$ adenosine receptors," Naunyn-Schmiedeberg's Archives of Pharmacology, vol. 360, No. 2, Aug. 1999 (pp. 103-108).

Koch et al., "Impaired Cognition after Stimulation of $P2Y_1$ Receptors in the Rat Medial Prefrontal Cortex," Neuropsychopharmacology, vol. 40, No. 2, Jan. 2015 (pp. 305-314).

Kumar et al., "5'-Phosphate and 5'-Phosphonate Ester Derivatives of (N)-Methanocarba Adenosine with in Vivo Cardioprotective Activity," Journal of Medicinal Chemistry, vol. 56, No. 3, Jan. 2013 (pp. 902-914).

Kwon et al., "Blockade of Peripheral $P2Y_1$ Receptors Prevents the Induction of Thermal Hyperalgesia via Modulation of $TRPV_1$ Expression in Carrageenan-Induced Inflammatory Pain Rats: Involvement of p38 MAPK Phosphorylation in DRGs,".Neuropharmacology, vol. 79, Dec. 2013 (pp. 368-379).

Lee et al., "Ring-Constrained (N)-Methanocarba Nucleosides as Adenosine Receptor Agonists: Independent 5'-Uronamide and 2'-Deoxy Modifications," Bioorganic & Medicinal Chemistry Letters, vol. 11, No Month Listed 2001 (pp. 1333-1337).

Lewerenz et al., "$A_3$ Receptors in Cortical Neurons: Pharmacological Aspects and Neuroprotection during Hypoxia," Drug Development Research, vol. 58, 2003 (pp. 420-427).

Liang et al., "A physiological role of the adenosine $A_3$ receptor: Sustained cardioprotection," The Proceedings of the National Academy of Science, U.S.A., vol. 95, No. 12, Jun. 1998 (pp. 6995-6999).

Little et al., "Endogenous adenosine A3 receptor activation selectively alleviates persisent pain states," Brain Advance Access published Nov. 19, 2015; (pp. 1-8).

Lubitz et al., "Adenosine $A_3$ receptor stimulation and cerebral ischemia," European Journal of Pharmacology, vol. 263, No Month Listed 1994 (pp. 59-67).

Lubitz et al., "Chronic administration of adenosine $A_3$ receptor agonist and cerebral ischemia: neuronal and glial effects," European Journal of Pharmacology, vol. 367, No. Month Listed 1999 (pp. 157-163).

Lubitz et al., "Right Thing at a Wrong Time? Adenosine $A_3$ Receptors and Cerebroprotection in Stroke," Annals New York Academy of Sciences, Neuroprotective Agents: Fifth International Conference, vol. 939, Jun. 2001 (pp. 85-96).

Marie et al., "Differential functional role of purinergic and nitrergic inhibitory co-transmitters in human colonic relaxation," Acta Physiologica, vol. 212, No. 4, Oct. 2014 (pp. 293-305).

(56) References Cited

OTHER PUBLICATIONS

Muller et al., "Recent developments in adenosine receptor ligands and their potential as novel drugs," Biochimica et Biophysica Acta, vol. 1808, vol. 5, May 2011 (pp. 1290-1308).
Nayak et al., "Synthesis and Anti-Renal Fibrosis Activity of Conformationally Locked Truncated 2-Hexynyl-$N^6$-Substituted-(N)-Methanocarba-nucleosides as $A_3$ Adenosine Receptor Antagonists and Partial Agonists," Journal of Medicinal Chemistry, vol. 57,.no. 4, Jan. 2014 (pgs. 1344-1354).
Paoletta et al., "Rational Design of Sulfonated $A_3$ Adenosine Receptor-Selective Nucleosides as Pharmacological Tools to Study Chronic Neuropathic Pain," Journal of Medicinal Chemistry, vol. 56, No. 14, Jun. 2013 (pp. 5949-5963).
Perreira et al., "'Reversine' and its 2-Substituted Adenine Derivates as Potent and Selective $A_3$ Adenosine Receptor Antagonists," The Journal of Medicinal Chemistry, vol. 48, No. 15, Jul. 2005 (pp. 4910-4918).
PUBCHEM, "Compound Summary for CID 69572716, SCHEMBL5803724," retrieved from <<https://pubchem.ncbi.nlm.nih.gov/compound/69572716#section=Top>> accessed on Mar. 17, 2017 (10 pages).
Pugliese et al., "Role of adenosine $A_3$ receptors on CA1 hippocampal neurotransmission during oxygen-glucose deprivation episodes of different duration," Biochemical Pharmacology, vol. 74, No. 5, Sep. 2007 (pp. 768-779).
Ravi et al., "Adenine Nucleotide Analogues Locked in a Northern Methanocarba Conformation: Enhanced Stability and Potency as $P2Y_1$ Receptor Agonists," Journal of Medicinal Chemistry, vol. 45, No. 10, May 2002 (pp. 2090-2100).
Tamada et al., "Calcium responses in subserosal interstitial cells of the guinea-pig proximal colon," Neurogastroenterology and motility: the official journal of the European Gastrointestinal Motility Society, vol. 26, No. 1, Jan. 2014 (pp. 115-123).
Tosh et al., "Click Modification in the $N^6$ Region of $A_3$ Adenosine Receptor-Selective Carbocyclic Nucleosides for Dendrimeric Tethering that Preserves Pharmacophore Recognition," Bioconjugate Chemistry, vol. 23, No. 2, Feb. 2012 (pp. 232-247).
Tosh et al., "Structural Sweet Spot for $A_1$ Adenosine Receptor Activation by Truncated (N)-Methanocarba Nucleosides: Receptor Docking and Potent Anticonvulsant Activity," Journal of Medicinal Chemistry, vol. 55, No. 18, Sep. 2012 (pp. 8075-8090).
Tosh et al., "Methanocarba ring as a ribose modification in ligands of G protein-coupled purine and pyrimidine receptors: synthetic approaches," MedChemComm, vol. 2013, No. 4, Dec. 2013 (pp. 619-630).
Toti et al., "Synthesis and Evaluation of $N^6$-Substituted Apioadenosines as Potential Adenosine $A_3$ Receptor modulators," Bioorganic & Medicinal Chemistry Journal, vol. 22, No. 15, Aug. 2014 (pp. 4257-4268).
Tracey et al., "Novel $N^6$-substituted adenosine 5'-N-methyluronamindes with high selectivity for human adenosine $A_3$ receptors reduce ischemic myocardial injury," American Journal of Physiology Heart and Circulatory Physiology, vol. 285, No. 6, Dec. 2003 (pp. H2780-H2787).
U.S. Appl. No. 16/095,282, filed Oct. 19, 2018 (147 pages).
U.S. Appl. No. 16/353,737, filed Mar. 14, 2019 (146 pages).
Verzijl et al., "Functional selectivity of adenosine receptor ligands," Purinergic Signalling, vol. 7, May 2011 (pp. 171-192).
Volpini et al., "Synthesis and biological evaluation of 2-alkynyl-$N^6$-methyl-5'-N-methylcarboxamidoadenosine derivatives as potent and highly selective agonists for the human adenosine $A_3$ receptor," Journal of Medicinal Chemistry, vol. 52, No. 23, Dec. 2009 (pp. 7897-7900).
Wan et al., "The $A_3$ adenosine receptor agonist CP-532,903 [$N^6$-(2,5-dichlorobenzyl)-3'-aminoadenosine-5'-N-methylcarboxamide] protects against myocardial ischemia/reperfusion injury via the sarcolemmal ATP-sensitive potassium channel," Journal of Pharmacology and Experimental Therapeutics, vol. 324, No. 1, Jan. 2008 (pp. 234-243).
Warden et al., "Guidelines for the pharmacologic treatment of neurobehavioral sequelae of traumatic brain injury," Journal of Neurotrauma, vol. 23, No. 10, Oct. 2006 (pp. 1468-1501).
Wei et al., "Activation of the $P2Y_1$ receptor induces apoptosis and inhibits proliferation of prostate cancer cells," Biochemical Pharmacology, vol. 82, No. 4, Aug. 2011 (pp. 418-425).
Wong et al., "Post exposure administration of A1 adenosine receptor agonists attenuates noise-induced hearing loss", Hearing Research, vol. 260, 2010 (pp. 81-88).
Ziganshin et al., "Characteristics of ecto-ATPase of Xenopus oocytes and the inhibitory actions of suramin on ATP breakdown," Pflugers Archiv: European journal of physiology, vol. 429, No. 3, Jan. 1995 (pp. 412-418).
International Search Report and Written Opinion issued in PCT/US2019/053076 dated Dec. 13, 2019 (8 pages).
Jacobson et al., "Historical and Current Adenosine Receptor Agonists in Preclinical and Clinical Development," Front Cell Neurosci., 2019, vol. 13, No. 124, 17 pages.
PubChem-CID-11623975, Create Date: Oct. 26, 2006, p. 2.

* cited by examiner

POLYMORPHIC COMPOUNDS AND USES THEREOF

CROSS-REFERENCE TO RELATED APPLICATIONS

This application claims the benefit of U.S. Provisional Patent Application No. 62/736,979, filed on Sep. 26, 2018; the entirety of which is hereby incorporated by reference.

FIELD OF THE INVENTION

The present invention relates to compounds and methods of use thereof for treating, ameliorating, or promoting recovery from certain conditions of the brain, central nervous system (CNS), or cardiovascular system such as a brain injury, a neurodegenerative condition, or cardiac ischemia.

BACKGROUND OF THE INVENTION

Brain injuries are a distressingly common medical condition and one of the leading causes of morbidity and mortality worldwide. The brain is particularly susceptible to injury as neurons have a limited capacity to repair. When an individual is born, the brain already has essentially all the neurons it will have in life. Unlike other cells in the body, neurons stop reproducing shortly after birth. If these cells are injured or die, they are not replaced, often culminating in the disabling and largely irreversible degradation of a person's cognitive and sensorimotor capacity. Conditions that result in nerve cell death and damage range from ischemic episodes (e.g., stroke) and trauma, to degenerative disorders (e.g., Alzheimer's disease).

Injury to the Central Nervous System (CNS) is a substantial cause of death and disability worldwide. For example, according to the CDC approximately 1.7 million people sustain a Traumatic Brain Injury (TBI) annually, costing the U.S. economy in excess of $60 billion per year in terms of medical costs and lost productivity (Finkelstein, E; Corso, P; Miller, T, *The Incidence and Economic Burden of Injuries in the United States*, Oxford University Press: New York, 2006). Additionally, stroke is the third leading cause of death in the U.S. with an estimated incidence of 795,000 cases annually, a major cause of disability, and costing the U.S. economy over $34 billion per year (NINDS, 2014; stroke.nih.gov; and Mozaffarian D, Benjamin E J, Go A S, et al. "Heart disease and stroke statistics-2015 update: a report from the American Heart Association," *Circulation.* 2015; e29-322).

In the acute setting, there is an opportunity to treat patients within 24 hours that can limit the extent of the damage. Immediately after an ischemic or hemorrhagic stroke, the site of insult in the brain typically contains a core of tissue that is irreversibly damaged, and then also an area of viable but at-risk tissue called the penumbra. During this period, the insufficient oxygen and glucose supply to brain cells results in further secondary injury to the penumbra. The lack of oxygen and glucose decreases energy production by cell mitochondria. An immediate effect of this energy depletion is failure of the ion pumps, which by elevating extracellular potassium ($K^+$) ions, results in waves of recurrent spreading depolarizations in brain tissue. At the same time, influx of sodium ($Na^+$) ions into cells, followed by chloride ($Cl^-$) ions, results in the swelling of cells due to osmotic pressure elevation, pressuring nearby neurons and their processes, ultimately leading to lysis (cell rupture) and inflammatory responses. In general, this disruption of ion homeostasis leads to excitotoxicity, cell swelling and cell death that extends damage to adjacent tissue and expands lesions by secondary mechanisms. There is a need for effective treatments during the initial 24 hours to protect the stressed brain cells. The propagation of brain damage in stroke is similar to that observed in other forms of brain injury such as trauma and concussions.

Beyond acute treatment, effective astrocyte function plays a key role in broader neurorestoration—in the period 24-96 hours following brain insult, in the period months-years in patients with neurodegeneration such as Alzheimer's, or most generally in aged individuals. The inability of brain cells to regenerate requires the remaining intact brain tissue to reorganize in an attempt to recover any loss of function. This potential for neural reorganization is diminished in older individuals.

GPCR receptors have been suggested to mediate cardioprotective effects. Therefore, there is potential to treat heart and cardiovascular conditions by similar mechanisms of action via modulation of these receptors.

There is urgent and compelling unmet medical need for more effective treatments for brain injuries, CNS injuries, heart and cardiovascular diseases, and related conditions, as well as promoting neurorestoration in patients having a neurodegenerative condition such as Alzheimer's.

SUMMARY OF THE INVENTION

It has now been found that compounds of the present invention, and compositions thereof, are useful for treating, ameliorating, or promoting recovery from certain conditions of the brain, central nervous system (CNS), or cardiovascular system such as a brain injury, a neurodegenerative condition, or cardiac ischemia. In general, freebase forms, and pharmaceutically acceptable compositions thereof, are useful for treating or lessening the severity of a variety of diseases or disorders as described in detail herein. Such compounds are represented by the chemical structure below, denoted as compound A:

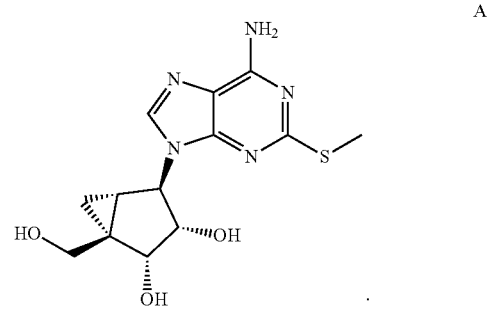 [SMILES: CSc1nc(N)c2ncn([C@H]3[C@H](O)[C@H](O)[C@]4(CO)C[C@H]34)c2n1]

Compounds of the present invention, and pharmaceutically acceptable compositions thereof, are useful for treating a variety of diseases, disorders or conditions, including those described herein.

DETAILED DESCRIPTION OF THE INVENTION

Figure 1:
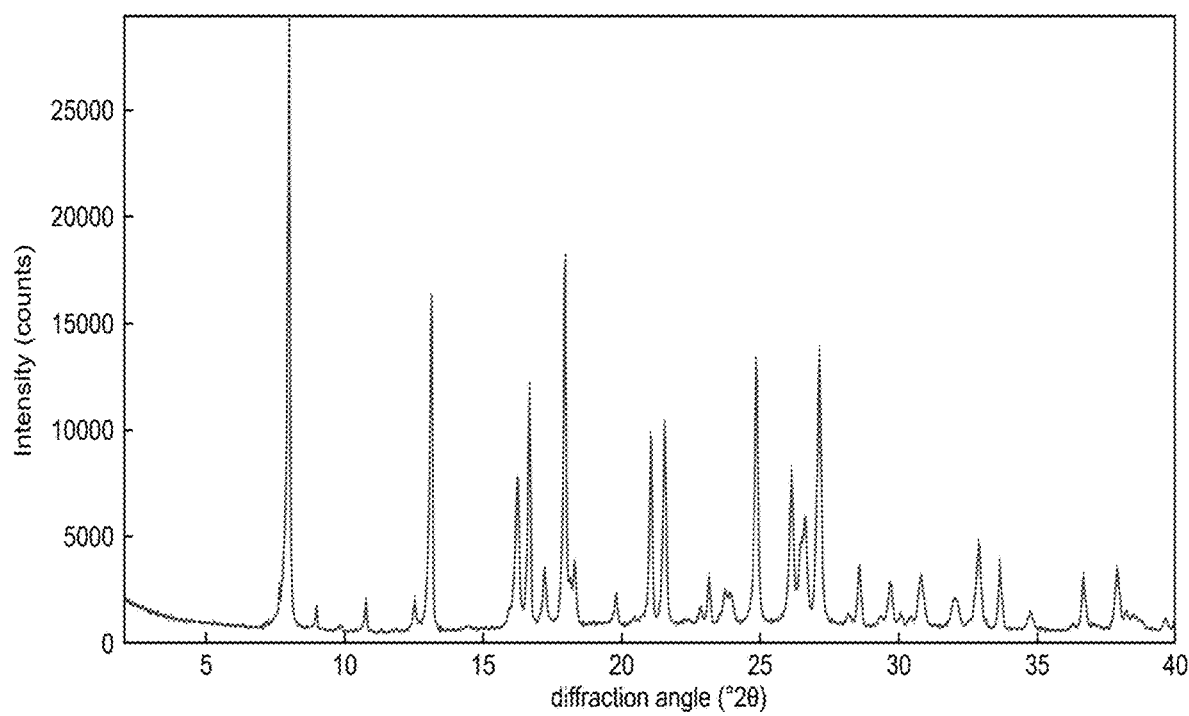
FIG. 1 depicts an XRPD pattern of Form A of compound A.

General Description of Certain Aspects of the Invention

U.S. Pat. No. 9,789,131, filed Apr. 21, 2011 and issued Oct. 17, 2017 ("the '131 patent"), the entirety of which is hereby incorporated herein by reference, and U.S. patent application Ser. No. 15/670,738, filed Aug. 7, 2017 and published as US 2018/0021363 on Jan. 25, 2018 ("the '363 publication"), the entirety of which is hereby incorporated herein by reference, describe certain therapeutically beneficial compounds. Such compounds include compound A:

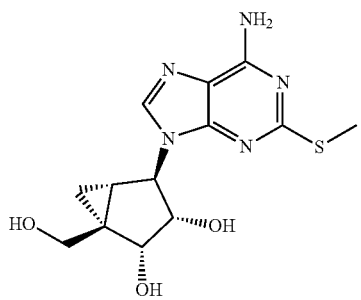

A

Compound A is designated as MRS4322 in the '131 patent and the synthesis of compound A is described in detail at Example 9 of the '131 patent, and is reproduced herein for ease of reference. Compound A is designated as MRS4322 in the '363 publication and the synthesis of compound A is described in detail at Example 9 of the '363 publication, and is reproduced herein for ease of reference.

It would be desirable to provide a solid form of compound A (e.g., as a freebase thereof) that imparts characteristics such as improved aqueous solubility, stability and ease of formulation. Accordingly, the present invention provides free base forms of compound A.

Free Base Forms of Compound A

It is contemplated that compound A can exist in a variety of physical forms. For example, compound A can be in solution, suspension, or in solid form. In certain embodiments, compound A is in solid form. When compound A is in solid form, said compound may be amorphous, crystalline, or a mixture thereof. Exemplary solid forms are described in more detail below.

In some embodiments, the present invention provides a form of compound A substantially free of impurities. As used herein, the term "substantially free of impurities" means that the compound contains no significant amount of extraneous matter. Such extraneous matter may include different forms of compound A, residual solvents, or any other impurities that may result from the preparation of, and/or isolation of, compound A. In certain embodiments, at least about 95% by weight of a form of compound A is present. In still other embodiments of the invention, at least about 99% by weight of a form of compound A is present.

According to one embodiment, a form of compound A is present in an amount of at least about 97, 97.5, 98.0, 98.5, 99, 99.5, 99.8 weight percent where the percentages are based on the total weight of the composition. According to another embodiment, a form of compound A contains no more than about 3.0 area percent HPLC of total organic impurities and, in certain embodiments, no more than about 1.5 area percent HPLC total organic impurities relative to the total area of the HPLC chromatogram. In other embodiments, a form of compound A contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for a form of compound A is also meant to include all tautomeric forms of compound A. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{11}$C-, $^{13}$C- or $^{14}$C-enriched carbon are within the scope of this invention.

It has been found that compound A can exist in a variety of solid forms. Exemplary such forms include polymorphs such as those described herein.

As used herein, the term "polymorph" refers to the different crystal structures into which a compound, or a salt or solvate thereof, can crystallize.

In certain embodiments, compound A is a crystalline solid. In other embodiments, compound A is a crystalline solid substantially free of amorphous compound A. As used herein, the term "substantially free of amorphous compound A" means that the compound contains no significant amount of amorphous compound A. In certain embodiments, at least about 95% by weight of crystalline compound A is present. In still other embodiments of the invention, at least about 99% by weight of crystalline compound A is present.

It has been found that compound A can exist in at least two distinct polymorphic forms. In certain embodiments, the present invention provides a polymorphic form of compound A referred to herein as Form A. In certain embodiments, the present invention provides a polymorphic form of compound A referred to herein as Form B.

In some embodiments, compound A is amorphous. In some embodiments, compound A is amorphous, and is substantially free of crystalline compound A.

Form A of Compound A

In some embodiments, Form A of compound A has at least 1, 2, 3, 4 or 5 spectral peak(s) selected from the peaks listed in Table 1 below.

TABLE 1

XRPD Peak Positions for Form A of Compound A

| °2θ[1] | Relative Intensity | °2θ | Relative Intensity | °2θ | Relative Intensity |
|---|---|---|---|---|---|
| 7.6 | 1.49 | 21.5 | 35.63 | 30.8 | 12.79 |
| 8.0 | 100 | 22.8 | 2.30 | 32.0 | 8.32 |
| 9.0 | 3.49 | 23.1 | 6.16 | 32.8 | 8.27 |
| 10.8 | 4.60 | 23.7 | 4.21 | 32.9 | 13.11 |
| 11.8 | 1.59 | 23.9 | 9.39 | 33.7 | 9.73 |
| 12.5 | 4.59 | 24.9 | 54.39 | 34.7 | 4.31 |
| 13.1 | 59.02 | 26.1 | 32.89 | 36.3 | 3.98 |
| 16.2 | 34.56 | 26.5 | 13.26 | 36.7 | 8.82 |
| 16.7 | 37.68 | 26.6 | 22.22 | 37.9 | 12.68 |
| 17.2 | 10.65 | 27.1 | 60.62 | 38.2 | 3.16 |
| 17.9 | 45.59 | 28.6 | 10.52 | 38.5 | 1.75 |
| 18.1 | 16.05 | 29.3 | 1.66 | 38.7 | 2.83 |
| 18.3 | 10.91 | 29.7 | 9.05 | 39.6 | 2.37 |
| 19.8 | 4.96 | 30.1 | 1.89 | — | — |
| 21.0 | 30.62 | 30.4 | 1.77 | — | — |

[1]In this and all subsequent tables, the position 2θ is within ± 0.2.

In some embodiments, Form A of compound A is characterized in that it has one or more peaks in its X-ray powder diffraction pattern selected from those at about 8.0 and about 13.1 degrees 2-theta. In some embodiments, Form A of compound A is characterized in that it has two peaks in its X-ray powder diffraction pattern selected from those at about 8.0 and about 13.1 degrees 2-theta. As used herein, the term "about," when used in reference to a degree 2-theta value, refers to the stated value ±0.2 degree 2-theta.

In certain embodiments, the X-ray powder diffraction pattern is substantially similar to the XRPD provided in FIG. 1.

Methods for preparing Form A of compound A are described infra.

Form B of Compound A

In some embodiments, Form B of compound A has at least 1, 2, 3, 4 or 5 spectral peak(s) selected from the peaks listed in Table 2 below.

TABLE 2

XRPD Peak Positions for Form B of Compound A

| °2θ[1] | Relative Intensity | °2θ | Relative Intensity | °2θ | Relative Intensity |
|---|---|---|---|---|---|
| 4.7 | 2.43 | 20.1 | 88.35 | 29.5 | 4.27 |
| 7.6 | 3.96 | 21.0 | 42.70 | 29.9 | 3.19 |
| 9.5 | 14.73 | 21.5 | 68.69 | 30.2 | 6.20 |
| 10.0 | 10.55 | 23.0 | 2.13 | 30.6 | 7.95 |
| 10.5 | 7.20 | 23.8 | 53.95 | 31.6 | 4.20 |
| 13.8 | 20.73 | 24.3 | 8.09 | 32.3 | 1.42 |
| 14.2 | 10.53 | 24.6 | 3.80 | 32.7 | 5.03 |
| 14.7 | 40.39 | 25.4 | 5.74 | 33.1 | 4.67 |
| 15.2 | 6.59 | 25.6 | 8.51 | 33.6 | 3.56 |
| 15.4 | 14.70 | 25.9 | 35.31 | 35.9 | 7.11 |
| 16.2 | 4.80 | 26.2 | 20.76 | 37.0 | 2.87 |
| 17.1 | 24.58 | 26.6 | 16.53 | 37.4 | 1.78 |
| 17.9 | 58.03 | 27.6 | 7.29 | 39.0 | 1.26 |
| 18.3 | 12.94 | 28.8 | 25.11 | — | — |
| 19.0 | 100 | 29.1 | 8.40 | — | — |

[1]In this and all subsequent tables, the position 2θ is within ± 0.2.

In some embodiments, Form B of compound A is characterized in that it has one or more peaks in its X-ray powder diffraction pattern selected from those at about 19.0, about 20.1 and about 21.5 degrees 2-theta. In some embodiments, Form B of compound A is characterized in that it has two or more peaks in its X-ray powder diffraction pattern selected from those at about 19.0, about 20.1 and about 21.5 degrees 2-theta. In some embodiments, Form B of compound A is characterized in that it has all three peaks in its X-ray powder diffraction pattern selected from those at about 19.0, about 20.1 and about 21.5 degrees 2-theta.

In some embodiments, Form B of compound A is characterized in that it has one or more peaks in its X-ray powder diffraction pattern selected from those at about 9.5, about 10.5 and about 13.8 degrees 2-theta. In some embodiments, Form B of compound A is characterized in that it has two or more peaks in its X-ray powder diffraction pattern selected from those at about 9.5, about 10.5 and about 13.8 degrees 2-theta. In some embodiments, Form B of compound A is characterized in that it has all three peaks in its X-ray powder diffraction pattern selected from those at about 9.5, about 10.5 and about 13.8 degrees 2-theta.

Figure 10:
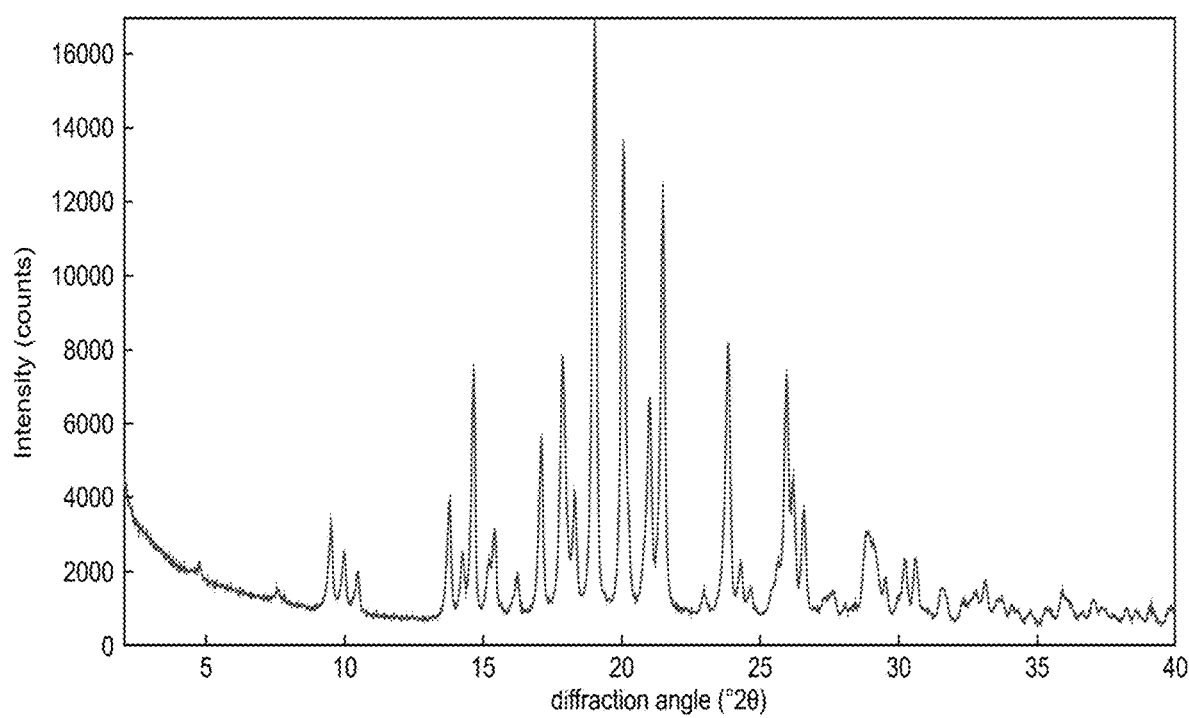
FIG. 10 depicts an XRPD pattern of Form B of compound A.

In certain embodiments, the X-ray powder diffraction pattern is substantially similar to the XRPD provided in FIG. 10.

Methods for preparing Form B of compound A are described infra.

In some embodiments, the present invention provides compound A:

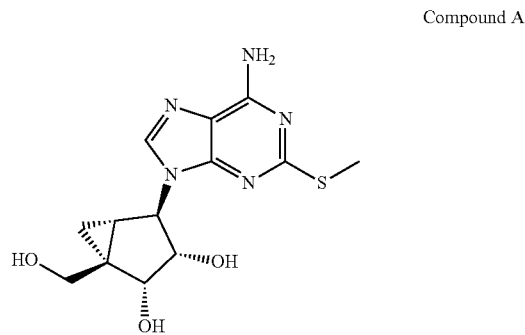 [SMILES: CSc1nc(N)c2ncn([C@H]3[C@H](O)[C@H](O)[C@]4(CO)C[C@H]34)c2n1]

Compound A wherein said compound is crystalline.

In some embodiments, the present invention provides a solid form of compound A, wherein said compound is substantially free of amorphous compound A.

In some embodiments, the present invention provides a solid form of compound A, wherein said compound is substantially free of impurities.

In some embodiments, the present invention provides a solid form of compound A, wherein said compound has one or more peaks in its XRPD selected from those at about 8.0 and about 13.1 degrees 2-theta. In some such embodiments, the present invention provides compound 1, wherein said compound has two peaks in its XRPD selected from those at about about 8.0 and about 13.1 degrees 2-theta. In some such embodiments, the present invention provides Compound A, wherein said compound is of Form A.

In some embodiments, the present invention provides a solid form of compound A, wherein said compound has an XRPD substantially similar to that depicted in FIG. 1.

In some embodiments, the present invention provides a solid form of compound A, wherein said compound has one or more peaks in its XRPD selected from those at about 19.0, about 20.1 and about 21.5 degrees 2-theta. In some such embodiments, the present invention provides compound A, wherein said compound has at least two peaks in its XRPD selected from those at about 19.0, about 20.1 and about 21.5 degrees 2-theta. In some embodiments, the present invention provides a solid form of compound A, wherein said compound has one or more peaks in its XRPD selected from those at about 9.5, about 10.5 and about 13.8 degrees 2-theta. In some such embodiments, the present invention provides compound A, wherein said compound has at least two peaks in its XRPD selected from those at about 0.5, about 10.5 and about 13.8 degrees 2-theta.

In some such embodiments, the present invention provides compound A, wherein said compound is of Form B.

In some embodiments, the present invention provides a solid form of compound A, wherein said compound has an XRPD substantially similar to that depicted in FIG. 10.

In some embodiments, the present invention provides a composition comprising a solid form of compound A and a pharmaceutically acceptable carrier or excipient.

In some embodiments, the present invention provides a compound selected from: compound A, Form A; and compound A, Form B.

In some embodiments, the present invention provides a method of inhibiting or preventing the accumulation of cAMP in a patient comprising administering to said patient a solid form of compound A, or a pharmaceutically acceptable composition comprising the same.

In some embodiments, the present invention provides a method of treating an injury, disease, or condition selected from traumatic brain injury (TBI), concussion, stroke, partial or total spinal cord transection, malnutrition, toxic neuropathies, meningoencephalopathies, neurodegeneration caused by a genetic disorder, age-related neurodegeneration, vascular disease, Alzheimer's Disease (AD), Parkinson's Disease (PD), Huntington's Disease (HD), Multiple Sclerosis (MS), amyotrophic lateral sclerosis (ALS), chronic traumatic encephalopathy (CTE), cardiovascular disease, autoimmune diseases, allergic diseases, transplant rejection, graft-versus-host disease, intraocular hypertension, glaucoma, odor sensitivity, an olfactory disorder, type 2 diabetes and/or pain control, respiratory diseases, deficits in CNS function, deficits in learning, deficits in cognition, otic disorders, Meniere's disease, endolymphatic hydrops, progressive hearing loss, dizziness, vertigo, tinnitus, collateral brain damage associated with radiation cancer therapy, migraine treatment, sleep disorders in the elderly, epilepsy, schizophrenia, symptoms experienced by recovering alcoholics, damage to neurons or nerves of the peripheral nervous system during surgery, gastrointestinal conditions, pain mediated by the CNS, migraine, collateral brain damage associated with radiation cancer therapy, depression, mood or behavioral changes, dementia, erratic behavior, suicidality, tremors, Huntington's chorea, loss of coordination of movement, deafness, impaired speech, dry eyes, hypomimia, attention deficit, memory loss, cognitive difficulties, vertigo, dysarthria, dysphagia, ocular abnormalities or disorientation, or addiction; comprising administering to a patient a solid form of compound A, or a pharmaceutically acceptable composition comprising the same. In some embodiments, the present invention provides a method of treating an injury, disease, or condition selected from traumatic brain injury (TBI), stroke, a neurodegenerative condition, or a heart or cardiovascular disease, comprising administering to a patient in need thereof an effective amount of an agonist of an $A_3$ adenosine receptor ($A_3R$). In some embodiments, the agonist of an $A_3$ adenosine receptor ($A_3R$) is a solid form of compound A, or a pharmaceutically acceptable composition comprising the same. In some embodiments, the agonist of an $A_3$ adenosine receptor ($A_3R$) is a solid form of compound A, or a pharmaceutically acceptable composition comprising the same. In some embodiments, a solid form of compound A, or a pharmaceutically acceptable composition comprising the same, acts by dual agonism at an $A_3$ adenosine receptor and an $A_1$ adenosine receptor ($A_1R$).

In some embodiments, the present invention provides a method of treating an injury, disease, or condition selected from traumatic brain injury (TBI), stroke, a neurodegenerative condition, or a heart or cardiovascular disease, comprising administering to a patient in need thereof an effective amount of a biased agonist, partial agonist, or biased partial agonist of an $A_3$ adenosine receptor ($A_3R$). In some embodiments, the biased agonist, partial agonist, or biased partial agonist of an $A_3$ adenosine receptor ($A_3R$) is a solid form of compound A, or a pharmaceutically acceptable composition comprising the same. In some embodiments, a solid form of compound A, or a pharmaceutically acceptable composition comprising the same, acts by dual agonism at an $A_3R$ and an $A_1R$.

In some embodiments, the present invention provides a method of treating a brain or central nervous system (CNS) injury or condition selected from traumatic brain injury (TBI) or stroke, comprising administering to a patient in need thereof an effective amount of a solid form of compound A, or a pharmaceutically acceptable composition comprising the same.

In some embodiments, the present invention provides a method of treating or ameliorating a traumatic brain injury (TBI), radiation damage, stroke, migraine headache, a heart or cardiovascular disease, or neurodegenerative disorder, comprising administering to a patient in need thereof an effective amount of a solid form of compound A, or a pharmaceutically acceptable composition comprising the same.

In some embodiments, the present invention provides a method of treating or ameliorating a traumatic brain injury (TBI), radiation damage, stroke, migraine headache, a heart or cardiovascular disease, or neurodegenerative disorder, comprising administering to a patient in need thereof an effective amount of a solid form of compound A, or a pharmaceutically acceptable composition comprising the same.

In some embodiments, the present invention provides a method of treating an injury, disease, or condition selected from traumatic brain injury (TBI), stroke, a neurodegenerative condition, or a heart or cardiovascular disease comprising administering to a patient in need thereof an effective amount of a solid form of compound A, or a pharmaceutically acceptable composition comprising the same.

In some embodiments, the injury, disease, or condition is TBI.

In some embodiments, the TBI is selected from concussion, blast injury, combat-related injury, or a mild, moderate or severe blow to the head.

In some embodiments, the injury, disease, or condition is a stroke selected from ischemic stroke, hemorrhagic stroke, subarachnoid hemorrhage, cerebral vasospasm, or transient ischemic attacks (TIA).

In some embodiments, neuroprotection or neurorestoration is increased in the patient as compared with an untreated patient.

In some embodiments, the neurodegenerative disease is selected from Alzheimer's Disease (AD), Parkinson's Disease (PD), Huntington's Disease (HD), Multiple Sclerosis (MS), amyotrophic lateral sclerosis (ALS), chronic traumatic encephalopathy (CTE), or a neurodegenerative condition caused by a virus, alcoholism, tumor, toxin, or repetitive brain injuries.

In some embodiments, the neurodegenerative disease is Parkinson's Disease.

In some embodiments, the injury, disease, or condition is Alzheimer's Disease, migraine, brain surgery, or a neurological side effect associated with cancer chemotherapy.

In some embodiments, the recovery period after the TBI, stroke, cardiac ischemia, or myocardial infarction is decreased as compared with an untreated patient.

In some embodiments, the heart or cardiovascular disease is selected from cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis.

In some embodiments, the heart or cardiovascular disease is cardiac ischemia or myocardial infarction.

In some embodiments, the compound or composition is administered chronically to treat stroke, cardiac ischemia, or myocardial infarction during the time period after the injury has occurred as it resolves.

In some embodiments, the present invention provides a method of increasing neuroprotection or neurorestoration in a patient in need thereof who has suffered a TBI or stroke, comprising administering to the patient an effective amount of a solid form of compound A, or a pharmaceutically acceptable composition comprising the same.

In some embodiments, the compound or pharmaceutically acceptable salt thereof is administered orally, intravenously, or parenterally.

In some embodiments, the compound or composition is administered within 24 hours of the TBI or stroke.

In some embodiments, the compound or composition is administered within 8 hours of the TBI or stroke.

In some embodiments, the compound or composition is administered at least during the first 8-48 hours following the TBI or stroke.

In some embodiments, the present invention provides a method of treating a heart or cardiovascular disease comprising administering to a patient in need thereof an effective amount of a solid form of compound A, or a pharmaceutically acceptable composition comprising the same.

In some embodiments, the patient has suffered a cardiac ischemia or myocardial infarction.

In some embodiments, the compound or composition increases cardioprotection or regeneration of damaged heart tissue in the patient.

In some embodiments, the compound or composition decreases the recovery period after the cardiac ischemia or myocardial infarction in the patient as compared with an untreated patient.

In some embodiments, the present invention provides a method of treating an injury, disease, disorder, or condition selected from:
  (i) brain damage caused by radiation or collateral brain damage associated with radiation cancer therapy or migraine treatment;
  (ii) migraine headache;
  (iii) a condition associated with a brain injury or a neurodegenerative condition; or
  (iv) an autoimmune disease or condition, glaucoma, an otic disorder, progressive hearing loss, tinnitus, epilepsy, pain control, pain mediated by the CNS, neuropathic pain, inflammatory pain, or acute pain;
comprising administering to a patient in need thereof an effective amount of a solid form of compound A, or a pharmaceutically acceptable composition comprising the same.

In some embodiments, the compound or composition increases neuroprotection or neurorestoration in the patient as compared with an untreated patient.

In some embodiments, the condition associated with a brain injury or a neurodegenerative condition is selected from epilepsy, migraine, collateral brain damage associated with radiation cancer therapy, depression, mood or behavioral changes, dementia, erratic behavior, suicidality, tremors, Huntington's chorea, loss of coordination of movement, deafness, impaired speech, dry eyes, hypomimia, attention deficit, memory loss, cognitive difficulties or deficit in cognition, deficit in CNS function, deficit in learning, vertigo, dysarthria, dysphagia, ocular abnormalities, or disorientation.

In some embodiments, the present invention provides a method of increasing cardioprotection or regeneration of damaged heart tissue in a patient in need thereof who has suffered a cardiac ischemia or myocardial infarction, comprising administering to the patient an effective amount of a solid form of compound A, or a pharmaceutically acceptable composition comprising the same.

In some embodiments, the present invention provides a method for preparing a solid form of compound A, comprising one or more steps of removing a solvent and adding a solvent. In some embodiments, an added solvent is the same as the solvent removed. In some embodiments, an added solvent is different from the solvent removed. Means of solvent removal are known in the synthetic and chemical arts and include, but are not limited to, any of those described herein and in the Exemplification.

In some embodiments, a method for preparing a solid form of compound A comprises one or more steps of heating or cooling a preparation.

In some embodiments, a method for preparing a solid form of compound A comprises one or more steps of agitating or stirring a preparation.

In some embodiments, a method for preparing a solid form of compound A comprises a step of heating.

In certain embodiments, a solid form of compound A precipitates from the mixture. In another embodiment, a solid form of compound A crystallizes from the mixture. In other embodiments, a solid form of compound A crystallizes from solution following seeding of the solution (i.e., adding crystals of compound A to the solution).

A solid form of Compound A can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, a solid form of compound A is optionally isolated. It will be appreciated that a solid form of compound A may be isolated by any suitable physical means known to one of ordinary skill in the art. In certain embodiments, precipitated a solid form of compound A is separated from the supernatant by filtration. In other embodiments, precipitated solid form of compound A is separated from the supernatant by decanting the supernatant.

In certain embodiments, a solid form of compound A is separated from the supernatant by filtration.

In certain embodiments, an isolated solid form of compound A is dried in air. In other embodiments, isolated solid form of compound A is dried under reduced pressure, optionally at elevated temperature.

Examples of suitable solvents useful in the present invention include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, the solvent is one or more organic alcohols. In some embodiments, the solvent is chlorinated. In some embodiments, the solvent is an aromatic solvent.

In certain embodiments, a suitable solvent is methanol, ethanol, isopropanol, or acetone wherein said solvent is anhydrous or in combination with water or heptane. In some embodiments, suitable solvents include tetrahydrofuran, dimethylformamide, dimethylsulfoxide, glyme, diglyme, methyl t-butyl ether, t-butanol, n-butanol, and acetonitrile. In some embodiments, a suitable solvent is ethanol. In some embodiments, a suitable solvent is anhydrous ethanol. In some embodiments, the suitable solvent is MTBE.

In some embodiments, a suitable solvent is ethyl acetate. In some embodiments, a suitable solvent is a mixture of methanol and methylene chloride. In some embodiments, a suitable solvent is a mixture of acetonitrile and water. In certain embodiments, a suitable solvent is methyl acetate, isopropyl acetate, acetone, or tetrahydrofuran. In certain embodiments, a suitable solvent is diethyl ether. In certain embodiments, a suitable solvent is water. In certain embodiments, a suitable solvent is methyl ethyl ketone. In certain embodiments, a suitable solvent is toluene.

Uses of Compounds and Pharmaceutically Acceptable Compositions Thereof

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent, delay or lessen the severity of their recurrence.

Brain, CNS, Cardiovascular, and Other Injuries and Conditions

In some embodiments, the present invention provides a new approach to preventing and/or treating brain damage associated with acute brain trauma as well as longer term diseases of the brain and CNS and heart and cardiovascular diseases and conditions. In one aspect, the present invention provides methods of treating such injuries, diseases, and conditions by utilizing neuroprotective and neurorestorative effects mediated by astrocytes, which are now understood as the key natural caretaker cell of neurons, as well as the astrocyte mitochondria, which supply a significant portion of the brain's energy. In another aspect, the present invention provides methods of treating such injuries, diseases, and conditions by cardioprotective and regenerative effects mediated by $A_3R$ receptors. Regarding neuroprotective and neurorestorative effects, without wishing to be bound by theory, it is believed that selective enhancement of astrocyte energy metabolism mediated by $A_3R$ and/or $P2Y_1$ receptors promotes astrocyte caretaker functions, such as their neuroprotective and neurorestorative functions, in turn enhancing the resistance of neurons and other cells to both acute injury and long term stress. In some cases, it may be advantageous to achieve biased, i.e., selective or preferential, of one or more pathways mediated by $A_3R$ and/or $P2Y_1$ and/or $A_1R$ receptors wherein one or more undesired pathways are not activated, or activated to a lesser degree. In addition to or as an alternative to astrocytes, neuroprotective or neurorestorative function of glia, microglia, neurons, endothelium cells and other brain and/or CNS cell types may be activated. Accordingly, in one aspect, the present invention provides compounds and methods of use thereof for treating, ameliorating, or promoting recovery from certain conditions of the brain or central nervous system (CNS) such as brain injuries, for example by increasing neuroprotection and/or neurorestorative effects mediated by astrocytes, glia, microglia, neurons, endothelium cells or other cells of the brain and/or CNS, comprising administering to a patient in need thereof an effective amount of a solid form of compound A, or a pharmaceutically acceptable composition comprising the same.

Astrocytes play key roles in supporting and protecting neurons and they critically affect the outcome of brain injuries that cause brain damage, such as ischemic injuries. The central role astrocyte mitochondria themselves play in these brain functions is less well appreciated. For example, inhibition of astrocyte mitochondria increases swelling and leads to necrotic cell death. Neurons are permanently injured by recurrent spreading depolarizations only if astrocyte mitochondrial function fails, and astrocyte mitochondria are required for reduction of pathophysiological elevations of extracellular $K^+$, which initiate spreading depolarizations. Activation of purinergic receptors on astrocytes results in increased mitochondrial $Ca^{2+}$ that enhances mitochondrial citric acid cycle function and increases respiration and ATP production. Accordingly, in one aspect, the present invention relates to the discovery that activation of astrocyte purinergic receptors enhances brain cell survival signalling pathways, enabling both astrocyte and neuronal viability during oxidative stress. Furthermore, activated astrocytes generate and supply reduced glutathione, a key antioxidant that aids in the resistance of both astrocytes and neurons to oxidative stress. Thus, in one aspect, the present invention provides a method of modulating astrocyte purinergic receptors to promote survival and viability of one or more cell types in the brain of a patient after oxidative stress, such as oxidative stress caused by a brain injury, ischemia-reperfusion or a neurodegenerative condition, comprising administering to a patient in need thereof a solid form of compound A, or a pharmaceutically acceptable composition comprising the same.

In some embodiments, activation of astrocytes is achieved through contacting with a disclosed compound one or more purinergic receptors such as adenosine receptors (ARs), for example those associated with or expressed by astrocytes, thus modulating the activity of the one or more receptors. In some embodiments, through effects on adenosine receptors such as $A_1$, $A_{2A}$, $A_{2B}$ and $A_3$ on astrocytes, the compound activates astrocytes to treat one or more disclosed diseases or conditions. In some embodiments, after administration to a patient in need thereof, a disclosed compound influences one or more functions such as glutamate uptake, reactive gliosis, swelling, and release of neurotrophic and neurotoxic factors having an impact on metabolic stress and its consequences, thus treating one or more diseases or conditions. In some embodiments, the compound is an AR agonist. In some embodiments, the purinergic receptor is an $A_3$ adenosine receptor ($A_3R$). In some embodiments, the compound is an $A_3R$ agonist. In some embodiments, the compound is a partial agonist or biased agonist or biased partial agonist, at an $A_3$ receptor ($A_3R$), such as a human $A_3$ receptor (hA3R). In some embodiments, the compound is a biased antagonist at an $A_3$ receptor. In some embodiments, the compound acts by dual agonism at an $A_3R$ and an $A_1R$. In some embodiments, the compound is a solid form of compound A, or a pharmaceutically acceptable composition comprising the same.

P2Y receptors are G-protein-coupled receptors and different subtypes of these receptors have important roles in processes such as synaptic communication, cellular differentiation, ion flux, vasodilation, blood brain barrier permeability, platelet aggregation and neuromodulation. Characterized members of the purinergic P2Y receptor family include the mammalian $P2Y_1$, $P2Y_{11}$, $P2Y_{12}$ and $P2Y_{13}$ receptors, which bind to adenine nucleotides; the $P2Y_4$, $P2Y_6$, and $P2Y_{14}$ receptors, that bind to uracil nucleotides; and the $P2Y_2$ and rodent $P2Y_4$ receptors, which have mixed selectivity. In some embodiments, activation of astrocytes is achieved through contacting with a disclosed compound one or more purinergic receptors such as P2Y receptors, for example those associated with or expressed by astrocytes, thus modulating the activity of the one or more receptors. In some embodiments, through effects on P2Y receptors such as $P2Y_1$, $P2Y_{11}$, $P2Y_{12}$ and $P2Y_{13}$ receptors associated with or expressed by astrocytes, the compound activates astrocytes to treat one or more disclosed diseases or conditions. In some embodiments, the P2Y receptor is a $P2Y_1$ receptor. In some embodiments, the $P2Y_1$ receptor is located on intracellular mitochondrial membranes. In some embodiments, the compound is a P2Y agonist. In some embodiments, the compound is a $P2Y_1$ agonist, e.g. at a human $P2Y_1$ receptor. In some embodiments, the compound is a biased agonist, partial agonist, or biased partial agonist at a $P2Y_1$ receptor, such as a human $P2Y_1$ receptor. In some embodiments, the compound is a biased antagonist at a $P2Y_1$ receptor. In some embodiments, the compound is a solid form of compound A, or a pharmaceutically acceptable composition comprising the same.

In another aspect, the present invention provides a method of treating or ameliorating a brain injury, such as a brain injury resulting from a TBI or progressive neurodegenerative disorder, in a patient in need thereof, comprising administering to the patient an effective amount of a disclosed compound. In some embodiments, the subject has suffered a TBI, concussion, stroke, partial or total spinal cord transection, or malnutrition. In other embodiments, the subject has suffered toxic neuropathies, meningoencephalopathies, neurodegeneration caused by a genetic disorder, age-related neurodegeneration, or a vascular disease; or another disease disclosed in U.S. Pat. No. 8,691,775, which is hereby incorporated by reference. In some embodiments, the present invention provides a method of treating or ameliorating a brain injury, such as a brain injury resulting from a TBI or progressive neurodegenerative disorder, in a patient in need thereof, comprising administering to the patient an effective amount of an $A_3R$ agonist. In other embodiments, the present invention provides a method of treating or ameliorating a brain injury, such as a brain injury resulting from a TBI or progressive neurodegenerative disorder, in a patient in need thereof, comprising administering to the patient an effective amount of a $P2Y_1$ agonist. In some embodiments, the compound is a biased agonist, partial agonist, or biased partial agonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

In another aspect, the present invention provides a method of promoting or increasing neuroprotection, neurorestoration, or neuroregeneration in a patient suffering from a disease or condition, comprising administering to the patient an effective amount of a disclosed compound, for example a solid form of compound A, or a pharmaceutically acceptable composition comprising the same. In some embodiments, the patient is suffering from a neurodegenerative disease or condition. In some embodiments, the patient has suffered a TBI.

In another aspect, the present invention provides a method of promoting astrocyte-mediated neuroprotection or neurorestoration in a patient in need thereof, comprising administering to the patient an effective amount of a disclosed compound. In some embodiments, the present invention provides a method of promoting astrocyte-mediated neuroprotection or neurorestoration in a patient in need thereof, comprising administering to the patient an effective amount of an $A_3R$ agonist. In other embodiments, the present invention provides a method of promoting astrocyte-mediated neuroprotection or neurorestoration in a patient in need thereof, comprising administering to the patient an effective amount of a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

In another aspect, the present invention provides a method of promoting survival of neurons, glial cells, endothelial cells or other brain cells, such as those in an ischemic penumbra in a patient in need thereof, comprising administering to the patient an effective amount of a compound disclosed herein. In some embodiments, the present invention provides a method of promoting survival of neurons, glial cells, or other brain cells, such as those in an ischemic penumbra in a patient in need thereof, comprising administering to the patient an effective amount of an $A_3R$ agonist. In some embodiments, the present invention provides a method of promoting survival of neurons, glial cells, endothelial cells or other brain cells, such as those in an ischemic penumbra in a patient in need thereof, comprising administering to the patient an effective amount of a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

In further embodiments, the patient has or is at risk of acquiring a brain injury such as those below. Accordingly, methods of treating the conditions discussed below are also provided.

Traumatic Brain Injuries

Traumatic brain injuries (TBI) are a distressingly common medical condition and are predicted to become the third major cause of global morbidity and mortality by 2020. There are no approved treatments for TBI, and most TBI patients are discharged from the hospital with no pharmacological treatment (Witt 2006). Repetitive TBI such as concussions can trigger age-associated neurodegeneration that results in a range of symptoms and disabilities over decades (McKee 2013). TBIs can happen through sports-related injuries, motor vehicle accidents, falls, explosive impacts, physical assaults, etc. Injuries range widely in their complexity and severity, from "mild" concussions with brief alterations in mental status, cognitive difficulties, or loss of consciousness to "severe" with prolonged periods of unconsciousness and/or amnesia after the injury. In the U.S., approximately 1.7 million people have an injury resulting in a TBI annually and seek medical intervention (USCSF and CDC), and the CDC estimates that 1.6 to 3.8 million additional concussion incidents occur in sports and other recreational pursuits annually that do not present to hospital or emergency departments. (CDC; Langlois 2006) Approximately 5-10% of athletes will receive a concussion each sport season. (Sports Concussion Institute 2012) Football is the sport with the highest concussion risk for males (75% chance for concussion), while soccer has the highest concussion risk for females (50% chance for concussion). TBI is the leading cause of death and disability in children and young adults (CDC) and the most commonly received military-related injury; approximately 20% of U.S. Service Members deployed since 2003 have sustained at least one TBI. (Chronic Effects of Neurotrauma Consortium (CENC); Warden 2006; Scholten 2012; Taylor 2012; Gavett 2011; Guskiewicz 2005; Omalu 2005) Total TBI-related indirect and direct medical costs are estimated at $77 billion annually (UCSF and CDC). At least 5 million Americans require ongoing daily support in performing activities as a result of TBI (CDC and Thurman 1999).

Activation of astrocytes according to the present invention represents a new treatment option for such conditions. Accordingly, provided herein in one aspect is a method of treating TBI or promoting recovery from TBI, comprising administering to a patient in need thereof an effective amount of a disclosed compound. In some embodiments, the TBI is selected from traumatic injuries to the brain (such as concussion, blast injury, combat-related injury) or spinal cord (such as partial or total spinal cord transection). In some embodiments, the TBI results from a mild, moderate, or severe blow to the head, comprises an open or closed head wound, or results from a penetrating or non-penetrating blow to the head. In some embodiments, the present invention provides a method of treating TBI or promoting recovery from TBI, comprising administering to a patient in need thereof an effective amount of an $A_3R$ agonist. In some embodiments, the present invention provides a method of treating TBI or promoting recovery from TBI, comprising administering to a patient in need thereof an effective amount of a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

Stroke

A stroke occurs when a blood vessel that transports oxygen and nutrients to the brain is disrupted due to an ischemic blockage or from the hemorrhagic rupture of a blood vessel in the brain, causing neurons, glia and endothelial cells in the disrupted region of the brain to die. The outcome of the stroke depends upon the location and breadth of damage, and the impacts of that damage are observed in the body functions regulated by the damaged brain region. Strokes can cause unilateral or bilateral paralysis, speech and language disabilities, memory loss, behavioural changes, and even death. Stroke is the fourth leading cause of death in the United States and is a major cause of adult disability. Each year, ~800,000 people experience a new or recurrent stroke. Each day, over 2000 Americans will have a stroke, resulting in death in over 400 of these incidents. Stroke accounted for ~1 of every 19 deaths in the United States in 2010. An estimated 6.8 million Americans ≥20 years of age has had a stroke. (AHA and Go 2014) As of 2010, the annual direct and indirect cost of stroke was estimated at $36.5 billion. Within minutes of a stroke, the lack of blood flow will permanently damage a core of brain tissue. Between this damaged core and normal brain tissue is a region of tissue known as the penumbra—tissue that is under gradated stress from lessened blood flow and some disruption of energy metabolism. Over the first 24-48 hours following a stroke incident, the stress on neuronal and glia cells in the penumbra resolves either with some recovery or further cell death.

In one aspect, the present invention provides a method of neuroprotective therapy in a stroke patient, comprising administering to a patient in need thereof an effective amount of a disclosed compound. In some embodiments, such therapy salvages as much of the penumbra as possible, and/or limits further acute tissue damage, and/or promotes neuron recovery. In another aspect is provided a method of treating stroke or promoting recovery from stroke, comprising administering to a patient in need thereof an effective amount of a disclosed compound. In another aspect is provided a method of promoting or increasing neuroprotection, neuroregeneration, or neurorestoration in a patient who has suffered a stroke, comprising administering to the patient an effective amount of a disclosed compound. In another aspect is provided a method of treating stroke or promoting recovery from stroke, comprising administering to a patient in need thereof an effective amount of an $A_3R$ agonist. In some embodiments, the present invention provides a method of treating stroke or promoting recovery from stroke, comprising administering to a patient in need thereof an effective amount of a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

In some embodiments, the stroke is selected from selected from ischemic stroke, hemorrhagic stroke, subarachnoid hemorrhage, cerebral vasospasm, or transient ischemic attacks (TIA). In some embodiments, the stroke is ischemic. In some embodiments, the stroke is hemorrhagic. In some embodiments, the compound is administered within 48 hours of the stroke. In some embodiments, the compound is administered within 24 hours of the stroke. In some embodiments, the compound is administered within 16 hours of the stroke. In some embodiments, the compound is administered within 8, 4, 2, or 1 hours of the stroke. In some embodiments, the compound is administered for at least the first 1-72 hours following the stroke. In some embodiments, the compound is administered for at least the first 8-52 hours following the stroke. In some embodiments, the compound is administered for at least the first 8-48 hours following the stroke. In some embodiments, the compound is administered for at least the first 24-48 hours following the stroke. In some embodiments, the compound is administered chronically to treat the stroke as it occurs. In some embodiments, the compound is administered chronically to treat Transient Ischemic Attacks (TIA).

In some embodiments, the compound is administered chronically to treat ischemic stroke, hemorrhagic stroke, a subarachnoid hemorrhage, cerebral vasospasm, transient ischemic attacks (TIA), or treat a patient who is at an increased risk for a stroke, such as a patient who has had a stroke in the past and is at risk for a further stroke, such as a patient over the age of 40, 45, 50, 55, 60, 65, 70, 75, or 80 years of age.

In some embodiments, the compound treats an ischemia-reperfusion injury caused by the stroke.

Neurodegenerative Diseases

Neurodegenerative diseases are incurable, progressive, and ultimately debilitating syndromes resulting from the progressive degeneration and/or death of neurons in the brain and spinal cord. Neurodegeneration results in movement (ataxias) and/or cognitive function (dementias) disorders, and includes a spectrum of diseases such as Alzheimer's Disease (AD), Parkinson's Disease (PD), Huntington's Disease (HD), Multiple Sclerosis (MS), amyotrophic lateral sclerosis (ALS), and chronic traumatic encephalopathy (CTE). While many neurodegenerative diseases are principally genetic in origin, other causes can include viruses, alcoholism, tumors or toxins, and as is now clear, repetitive brain injuries.

Neurons accumulate cellular damage over time due to the foregoing factors, which is generally considered the reason why many neurodegenerative diseases associated with prolonged cellular stress, such as Alzheimer's disease and Parkinson's disease, occur in aged individuals. Dementias represent the predominant outcome of neurodegenerative diseases with AD representing approximately 60-70% of cases. (Kandale 2013) As discussed above, activation of neuroprotective and neurorestorative mechanisms can ameliorate the progression of one or more neurodegenerative diseases. Accordingly, in one aspect the present invention provides a method of treating a neurodegenerative disease or promoting recovery from a neurodegenerative disease, comprising administering to a patient in need thereof an effective amount of a solid form of compound A, or a pharmaceutically acceptable composition comprising the same.

In one aspect, the present invention provides a method of promoting neuroprotection or neurorestoration in a patient suffering from a neurodegenerative disease, comprising administering to the patient an effective amount of a disclosed compound. In some embodiments is provided a method of promoting neuroprotection or neurorestoration in a patient suffering from a neurodegenerative disease, comprising administering to the patient an effective amount of an $A_3R$ agonist. In other embodiments is provided a method of promoting neuroprotection or neurorestoration in a patient suffering from a neurodegenerative disease, comprising administering to the patient an effective amount of a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

Alzheimer's Disease (AD)

An estimated 5.2 million Americans of all ages had AD in 2014; 11% of the population age 65 and older have AD. (Alzheimer's Association) By 2050, the number of people age 65 and older with AD is projected to nearly triple to a projected 13.8 million. In the U.S., the cost of providing care for AD patients is about $214 billion per year; 70% of this cost is covered by Medicare and Medicaid. The current trends would project these costs to grow to $1.2 trillion per year by 2050.

Activation of astrocytes and promoting neuroprotection and neurorestoration according to the present invention represents a new treatment option for AD. Accordingly, provided herein in one aspect is a method of treating AD or promoting neuroprotection or neurorestoration in a patient suffering from AD, comprising administering to the patient an effective amount of a compound disclosed herein. In some embodiments, the present invention provides a method of treating AD or promoting neuroprotection or neurorecovery in a patient suffering from AD, comprising administering to the patient an effective amount of an $A_3R$ agonist. In some embodiments, the present invention provides a method of treating AD or promoting neuroprotection or neurorecovery in a patient suffering from AD, comprising administering to the patient an effective amount of a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

Parkinson's Disease (PD)

As many as one million Americans live with PD, and each year approximately 60,000 Americans are newly diagnosed not including the thousands of cases that go undetected. (Parkinson's Disease Foundation) The total combined direct and indirect cost of PD, including medical treatment, social security payments and lost income, is estimated to be nearly $25 billion per year in the United States. (Parkinson's Disease Foundation and Huse 2005)

Activation of neuroprotection and neurorestoration according to the present invention represents a new treatment option for PD. Accordingly, provided herein in one aspect is a method of treating PD or promoting neuroprotection or neurorestoration in a patient suffering from PD, comprising administering to the patient an effective amount of a disclosed compound. In some embodiments, the present invention provides a method of treating PD or promoting neuroprotection or neurorecovery in a patient suffering from PD, comprising administering to the patient an effective amount of an $A_3R$ agonist. In some embodiments, the present invention provides a method of treating PD or promoting neuroprotection or neurorecovery in a patient suffering from PD, comprising administering to the patient an effective amount of a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

Multiple Sclerosis (MS)

More than 400,000 people in the United States have MS. In young adults, MS represents the most prevalent disease of the central nervous system. (Multiple Sclerosis Foundation) There is potential for astrocytes to reverse the destruction of nerve cell myelin coatings that is caused by MS by their neurorestorative effects and promotion of healing in the damaged CNS of MS patients.

Activation of neuroprotection and neurorestoration in the CNS according to the present invention thus represents a new treatment option for MS. Accordingly, provided herein in one aspect is a method of treating MS or promoting neuroprotection or neurorestoration in a patient suffering from MS, comprising administering to the patient an effective amount of a disclosed compound. In some embodiments, the present invention provides a method of treating MS or promoting neuroprotection or neurorecovery in a patient suffering from MS, comprising administering to the patient an effective amount of an $A_3R$ agonist. In some embodiments, the present invention provides a method of treating MS or promoting neuroprotection or neurorecovery in a patient suffering from MS, comprising administering to the patient an effective amount of a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

Amyotrophic Lateral Sclerosis (ALS)/Lou Gehrig's Disease

Approximately 5,600 people in the U.S. are diagnosed with ALS each year; as many as 30,000 Americans may have the disease concurrently. (ALS Association) Activation of astrocytes can provide stimulation of recovery and repair of the neurons and their connections in an ALS patient.

Accordingly, provided herein in one aspect is a method of treating ALS or promoting neuroprotection or neurorestoration in a patient suffering from ALS, comprising administering to the patient an effective amount of a disclosed compound. Also provided in other embodiments is a method of stimulating recovery and repair of the neurons and their connections in an ALS patient, comprising administering to the patient an effective amount of a compound disclosed herein. In some embodiments, the present invention provides a method of treating ALS or promoting neuroprotection or neurorecovery in a patient suffering from ALS, comprising administering to the patient an effective amount of an $A_3R$ agonist. In some embodiments, the present invention provides a method of treating ALS or promoting neuroprotection or neurorecovery in a patient suffering from ALS, comprising administering to the patient an effective amount of a $P2Y_1$ agonist. In some embodiments, the compound is a biased agonist, partial agonist, or biased partial agonist or antagonist at an $A_3$ receptor In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

Chronic Traumatic Encephalopathy (CTE)

CTE (a form of tauopathy) is a progressive neurodegenerative disease found in individuals who have suffered one or more (often multiple, or repeated over the course of time) severe blows to the head. CTE is most often diagnosed in professional athletes in American football, soccer, hockey, professional wrestling, stunt performing, bull riding and rodeo performing, motocross, and other contact sports who have experienced brain trauma and/or repeated concussions. A subset of CTE sufferers have chronic traumatic encephalomyopathy (CTEM), which is characterized by motor neuron disease symptoms that mimic ALS. Progressive muscle weakness and motor and gait abnormalities are believed to be early signs of CTEM. First stage symptoms of CTE include progressive attention deficit, disorientation, dizziness, and headaches. Second stage symptoms comprise memory loss, social instability, erratic behavior, and poor judgment. In third and fourth stages, patients suffer progressive dementia, slowed movements, tremors, hypomimia, vertigo, speech impediments, hearing loss, and suicidality, and may further include dysarthria, dysphagia, and ocular abnormalities, e.g. ptosis.

Accordingly, provided herein in one aspect is a method of treating or preventing CTE or promoting neuroprotection or neurorestoration in a patient suffering from CTE, comprising administering to the patient an effective amount of a disclosed compound. Also provided in other embodiments is a method of stimulating recovery and repair of the neurons and their connections in a CTE patient, comprising administering to the patient an effective amount of a disclosed compound. In some embodiments, the compound treats one or more symptoms of first stage, second stage, third stage, or fourth stage CTE. In some embodiments, the present invention provides a method of treating CTE or promoting neuroprotection or neurorecovery in a patient suffering from CTE, comprising administering to the patient an effective amount of an $A_3R$ agonist. In some embodiments, the present invention provides a method of treating CTE or promoting neuroprotection or neurorecovery in a patient suffering from CTE, comprising administering to the patient an effective amount of a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

On a microscopic scale the pathology includes neuronal death, tau deposition, TAR DNA-binding Protein 43 (TDP 43) beta-amyloid deposition, white matter changes, and other abnormalities. Tau deposition includes the increasing presence of dense neurofibrillary tangles (NFT), neurites, and glial tangles, which are made up of astrocytes and other glial cells. Thus, in some embodiments, the method treats, enhances clearance or prevents neuronal death, tau deposition, TAR DNA-binding Protein 43 (TDP 43) beta-amyloid deposition, white matter changes, and other abnormalities associated with CTE.

In some embodiments, the present invention provides long-term administration of a compound disclosed herein, such as a biased agonist, partial agonist, or biased partial agonist of $A_3R$, or a dual agonist at an $A_3R$ and an $A_1R$, or a biased agonist, partial agonist, or biased partial agonist of $P2Y_1$, to treat a neurodegenerative disease, such as those discussed above and below.

Cardiovascular Diseases

Disclosed compounds are also useful in treating a variety of cardiovascular diseases and conditions. In some embodiments, the present invention provides a method of treating a heart (cardiac) or cardiovascular disease, such as cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis, comprising administering an effective amount of a disclosed compound to a patient in need thereof, such as a solid form of compound A, or a pharmaceutically acceptable composition comprising the same. In some embodiments, a disclosed compound provides for modulation of ATP-sensitive potassium channels, for example via biased agonism, partial agonism, or biased partial agonism at an $A_3R$ receptor, or dual agonism at an $A_3R$ and an $A_1R$.

In some embodiments, the heart or cardiovascular disease is cardiac ischemia or myocardial infarction.

In some embodiments, the present invention provides a method of promoting or increasing cardioprotection, cardiorestoration, or cardioregeneration in a patient suffering from a heart (cardiac) or cardiovascular disease or condition, comprising administering to the patient an effective amount of a disclosed compound, for example a solid form of compound A, or a pharmaceutically acceptable composition comprising the same.

In some embodiments, the heart (cardiac) or cardiovascular disease from which the patient is suffering is cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis.

In some embodiments, a disclosed compound provides for modulation of ATP-sensitive potassium channels, for example via biased agonism, partial agonism, or biased partial agonism at an $A_3R$ receptor, or dual agonism at an $A_3R$ and an $A_1R$.

Other Diseases

Compounds that modulate beneficial effects such as neuroprotection, for example by increasing astrocyte mitochondrial activity, also have the potential to treat a variety of other diseases. For example, due to the role of astrocytes in neuroprotection disclosed in the present invention, activation of astrocytes, for example via modulation of $A_3R$ and/or a $P2Y_1$ receptor, may be useful in treating various diseases and conditions discussed below.

Accordingly, in some embodiments, the present invention provides a method of treating neurodegeneration in a patient suffering from a disease or condition, comprising administering to the patient an effective amount of a disclosed compound, for example a solid form of compound A, or a pharmaceutically acceptable composition comprising the same.

In some embodiments, the present invention provides a method of promoting or increasing neuroprotection, neurorestoration, or neuroregeneration in a patient suffering from a disease or condition, comprising administering to the patient an effective amount of a disclosed compound, for example a solid form of compound A, or a pharmaceutically acceptable composition comprising the same.

In some embodiments, the disease or condition is selected from autoimmune diseases, allergic diseases, and/or transplant rejection and graft-versus-host disease (for the use of certain nucleoside and nucleotide compounds in treating these conditions, see, for example, WO 2007/20018, hereby incorporated by reference). In other embodiments, the disease or condition is selected from intraocular hypertension and/or glaucoma (for the use of certain nucleoside and nucleotide compounds in treating these conditions, see, for example, WO 2011/77435, hereby incorporated by reference). In other embodiments, the disease or condition is selected from odor sensitivity and/or an olfactory disorder (for the use of certain nucleoside and nucleotide compounds in treating these conditions, see, for example, EP1624753, hereby incorporated by reference). In other embodiments, the disease or condition is selected from type 2 diabetes and/or pain control (for the use of certain nucleoside and nucleotide compounds in treating these conditions, see, for example, US 2010/0256086, hereby incorporated by reference).

In other embodiments, the disease or condition is selected from respiratory diseases and/or cardiovascular (CV) diseases (for the use of certain nucleoside and nucleotide compounds in treating these conditions, see, for example, FASEB J. (2013) 27:1118.4 (abstract of meeting), hereby incorporated by reference). In other embodiments, the disease or condition is selected from deficits in CNS function, deficits in learning and/or deficits in cognition (for the use of certain nucleoside and nucleotide compounds in treating these conditions, see, for example, Neuropsychopharmacology. 2015 January; 40(2):305-14. doi: 10.1038/npp.2014.173. Epub 2014 Jul. 15. "Impaired cognition after stimulation of a $P2Y_1$ receptor in the rat medial prefrontal cortex," Koch, H. et al. PMID: 25027332, hereby incorporated by reference). In other embodiments, the disease or condition is selected from a neurodegenerative disease such as Alzheimer's disease, Parkinson's disease, Huntington's disease, prion disease, and/or amyotrophic lateral sclerosis (for the use of certain nucleoside and nucleotide compounds in treating these conditions, see, for example, U.S. Pat. No. 8,691,775, hereby incorporated by reference). In other embodiments, the disease or condition is selected from otic disorders, Meniere's disease, endolymphatic hydrops, progressive hearing loss, dizziness, vertigo, tinnitus, collateral brain damage associated with radiation cancer therapy, and/or migraine treatment (for the use of certain nucleoside and nucleotide compounds in treating these conditions, see, for example, US 2009/0306225; UY31779; and U.S. Pat. No. 8,399,018, each of which is hereby incorporated by reference). In other embodiments, the disease or condition is selected from pathological sleep perturbations, depression, sleep disorders in the elderly, Parkinson's disease, Alzheimer's disease, epilepsy, schizophrenia, and/or symptoms experienced by recovering alcoholics (for the use of certain nucleoside and nucleotide compounds in treating these conditions, see, for example, US 2014/0241990, hereby incorporated by reference). In other embodiments, the disease or condition is selected from damage to neurons or nerves of the peripheral nervous system during surgery (for the use of certain nucleoside and nucleotide compounds in treating these conditions, see, for example, U.S. Pat. No. 8,685,372, hereby incorporated by reference). In other embodiments, the disease or condition is a cancer such as prostate cancer (for the use of certain nucleoside and nucleotide compounds in treating these conditions, see, for example, Biochem Pharmacol. 2011 Aug. 15; 82(4): 418-425. doi:10.1016/j.bcp.2011.05.013. "Activation of the P2Y1 Receptor Induces Apoptosis and Inhibits Proliferation of Prostate Cancer Cells," Qiang Wei et al., hereby incorporated by reference). In other embodiments, the disease or condition is selected from one or more gastrointestinal conditions such as constipation and/or diarrhea (for the use of certain nucleoside and nucleotide compounds in treating these conditions, see, for example, Acta Physiol (Oxf). 2014 December; 212(4):293-305. doi: 10.1111/apha.12408. "Differential functional role of purinergic and nitrergic inhibitory cotransmitters in human colonic relaxation," Mañé N1, Gil V, Martínez-Cutillas M, Clavé P, Gallego D, Jiménez M.; and Neurogastroenterol. Motil. 2014 January; 26(1):115-23. doi: 10.1111/nmo.12240. Epub 2013 Oct. 8. "Calcium responses in subserosal interstitial cells of the guinea-pig proximal colon," Tamada H., Hashitani H. PMID: 24329947, hereby incorporated by reference). In other embodiments, the disease or condition is selected from pain mediated by the CNS, such as neuropathic pain, inflammatory pain, and/or acute pain (for the use of certain nucleoside and nucleotide compounds in treating these conditions, see, for example, Br J Pharmacol. 2010 March; 159(5):1106-17. doi: 10.1111/j.1476-5381.2009.00596.x. Epub 2010 Feb. 5. "A comparative analysis of the activity of ligands acting at P2X and P2Y receptor subtypes in models of neuropathic, acute and inflammatory pain." Andó RD1, Méhész B, Gyires K, Illes P, Sperlágh B. PMID: 20136836), hereby incorporated by reference).

In other embodiments, the disease or condition is selected from cancer of the brain, such as glioblastoma (for the use of certain nucleoside and nucleotide compounds in treating these conditions, see, for example, Purinergic Signal. 2015 September; 11(3):331-46. doi: 10.1007/s11302-015-9454-7. Epub 2015 May 15. "Potentiation of temozolomide antitumor effect by purine receptor ligands able to restrain the in vitro growth of human glioblastoma stem cells." D'Alimonte, I. et al. PMID: 25976165, hereby incorporated by reference). In other embodiments, the disease or condition is pain (for the use of certain nucleoside and nucleotide compounds in treating pain, see, for example, Pharmacol Biochem Behav. 2015 January; 128:23-32. doi: 10.1016/j.pbb.2014.11.001. Epub 2014 Nov. 6. "Participation of peripheral $P2Y_1$, $P2Y_6$ and $P2Y_{11}$ receptors in formalin-induced inflammatory pain in rats." Barragán-Iglesias P. et al. PMID: 25449358; and Neuropharmacology. 2014 April; 79:368-79. doi: 10.1016/j.neuropharm.2013.12.005. Epub 2013 Dec. 12. "Blockade of peripheral $P2Y_1$ receptors prevents the induction of thermal hyperalgesia via modulation of TRPV1 expression in carrageenan-induced inflammatory pain rats: involvement of p38 MAPK phosphorylation in DRGs." Kwon S G, Roh D H, Yoon S Y, Moon J Y, Choi S R, Choi H S, Kang S Y, Han H J, Beitz A J, Lee J H. PMID: 24333674, each of which is hereby incorporated by reference). In other embodiments, the disease or condition is selected from a gastrointestinal disorder such as diarrhea (for the use of certain nucleoside and nucleotide compounds in treating these conditions, see, for example, Acta Physiol (Oxf). 2014 December; 212(4):293-305. doi: 10.1111/apha.12408. "Differential functional role of purinergic and nitrergic inhibitory cotransmitters in human colonic relaxation," Mañé N., Gil V, Martínez-Cutillas M, Clavé P, Gallego D, Jiménez M., hereby incorporated by reference). In other embodiments, the disease or condition is impaired cognition (for the use of certain nucleoside and nucleotide compounds in treating this condition, see, for example, Neuropsychopharmacology. 2015 January; 40(2):305-14. doi: 10.1038/npp.2014.173. Epub 2014 Jul. 15. "Impaired cognition after stimulation of $P2Y_1$ receptors in the rat medial prefrontal cortex," Koch H, Bespalov A, Drescher K, Franke H, Krügel U. PMID: 25027332, hereby incorporated by reference).

In some embodiments, the present invention provides a method of treating a disease or condition associated with brain injury or a neurodegenerative condition, such as epilepsy, migraine, collateral brain damage associated with radiation cancer therapy, depression, mood or behavioral changes, dementia, erratic behavior, suicidality, tremors, Huntington's chorea, loss of coordination of movement, deafness, impaired speech, dry eyes, hypomimia, attention deficit, memory loss, cognitive difficulties, vertigo, dysarthria, dysphagia, ocular abnormalities, or disorientation, comprising administering to a patient in need thereof an effective amount of a disclosed compound. In some embodiments, the compound is an $A_3R$ agonist. In some embodiments, the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

In further embodiments, the present invention provides a method of treating a neurodegenerative disease selected from the group consisting of Alzheimer's disease, Parkinson's disease, Huntington's disease, multiple sclerosis, amyotrophic lateral sclerosis, and prion disease in a patient in need thereof, comprising administering an effective amount of a disclosed compound. In some embodiments, the compound is an $A_3R$ agonist. In some embodiments, the compound is a $P2Y_1$ agonist. In some embodiments, the compound is a biased agonist, partial agonist, or biased partial agonist or antagonist at an $A_3$ receptor. In some embodiments, the compound acts by dual agonism at an $A_3R$ and an $A_1R$. In some embodiments, the compound is a biased agonist, partial agonist, or biased partial agonist or antagonist at a $P2Y_1$ receptor. In some embodiments, the compound is a solid form of compound A, or a pharmaceutically acceptable composition comprising the same.

In some embodiments, the improvement in cognitive or neurological function is measured as a score increase between about 1% and 20% in the delayed verbal recall task of the revised Wechsler Memory Scale. For example, the improvement in cognitive function may be measured as a score increase between about 1% and 10%, or between about 1% and 5%.

In some embodiments, the present invention provides a method of treating a brain or central nervous system (CNS) injury or condition selected from traumatic brain injury (TBI) or stroke, comprising administering to a patient in need thereof an effective amount of a solid form of compound A, or a pharmaceutically acceptable composition comprising the same.

In some embodiments, the brain or central nervous system (CNS) injury or condition is TBI. In some embodiments, the TBI is selected from concussion, blast injury, combat-related injury, or a mild, moderate or severe blow to the head.

In some embodiments, a solid form of compound A, or a pharmaceutically acceptable composition comprising the same, is administered within 24 hours of the TBI or stroke.

In some embodiments, a solid form of compound A, or a pharmaceutically acceptable composition comprising the same, is administered within 8 hours of the TBI or stroke.

In some embodiments, a solid form of compound A, or a pharmaceutically acceptable composition comprising the same, is administered at least during the first 8-48 hours following the TBI or stroke.

In some embodiments, the brain or central nervous system (CNS) injury or condition is stroke.

In some embodiments, a solid form of compound A, or a pharmaceutically acceptable composition comprising the same, is administered chronically to treat the stroke during the time period after the stroke has occurred as it resolves.

In some embodiments, neuroprotection or neurorestoration is increased in the patient as compared with an untreated patient.

In some embodiments, a solid form of compound A, or a pharmaceutically acceptable composition comprising the same, is a biased partial agonist at a human $A_3$ adenosine receptor ($A_3R$). In some embodiments, the compound acts by dual agonism at an $A_3R$ and an $A_1R$.

In some embodiments, the $A_3R$ is partially agonized in a manner biased toward neuroprotective functions of the $A_3R$ receptor.

In some embodiments, a solid form of compound A, or a pharmaceutically acceptable composition comprising the same, is administered orally, intravenously, or parenterally.

In one aspect, the present invention provides a method of increasing neuroprotection or neurorestoration in a patient who has suffered a TBI or stroke, comprising administering to a patient in need thereof an effective amount of a solid form of compound A, or a pharmaceutically acceptable composition comprising the same.

In some embodiments, the neuroprotection or neurorestoration decreases the recovery period after the TBI or stroke as compared with an untreated patient.

In some embodiments, a solid form of compound A, or a pharmaceutically acceptable composition comprising the same, is a biased partial agonist at a human $A_3$ adenosine receptor ($A_3R$) and the $A_3R$ is partially agonized in a manner biased toward neuroprotective functions of the $A_3R$ receptor. In some embodiments, the compound acts by dual agonism at an $A_3R$ and an $A_1R$.

In some embodiments, a solid form of compound A, or a pharmaceutically acceptable composition comprising the same, is administered orally, intravenously, or parenterally.

In one aspect, the present invention provides a method of treating an injury, disease, or condition selected from traumatic brain injury (TBI), stroke, a neurodegenerative condition, or a heart or cardiovascular disease, comprising administering to a patient in need thereof an effective amount of a solid form of compound A, or a pharmaceutically acceptable composition comprising the same.

In some embodiments, the injury, disease, or condition is TBI. In some embodiments, the TBI is selected from concussion, blast injury, combat-related injury, or a mild, moderate or severe blow to the head.

In some embodiments, the injury, disease, or condition is a stroke selected from ischemic stroke, hemorrhagic stroke, subarachnoid hemorrhage, cerebral vasospasm, or transient ischemic attacks (TIA).

In some embodiments, the neurodegenerative disease is selected from Alzheimer's Disease (AD), Parkinson's Disease (PD), Huntington's Disease (HD), Multiple Sclerosis (MS), amyotrophic lateral sclerosis (ALS), chronic traumatic encephalopathy (CTE), or a neurodegenerative condition caused by a virus, alcoholism, tumor, toxin, or repetitive brain injuries.

In some embodiments, the injury, disease, or condition is Parkinson's Disease.

In some embodiments, the injury, disease, or condition is Alzheimer's Disease, migraine, brain surgery, or a neurological side effect associated with cancer chemotherapy.

In some embodiments, the heart or cardiovascular disease is selected from cardiac ischemia, myocardial infarction, a cardiomyopathy, coronary artery disease, arrhythmia, myocarditis, pericarditis, angina, hypertensive heart disease, endocarditis, rheumatic heart disease, congenital heart disease, or atherosclerosis.

In some embodiments, the heart or cardiovascular disease is cardiac ischemia or myocardial infarction.

In some embodiments, a solid form of compound A, or a pharmaceutically acceptable composition comprising the same, is administered chronically to treat the stroke, cardiac ischemia, or myocardial infarction during the time period after the injury has occurred as it resolves.

In some embodiments, neuroprotection or neurorestoration is increased in the patient as compared with an untreated patient.

In some embodiments, the $A_3R$ is agonized in a biased manner toward neuroprotective functions of the $A_3R$ receptor via preferential activation of intracellular calcium mobilization with less, or no, activation of other $A_3R$-mediated pathways, or via preferential activation of Gq11-mediated intracellular calcium mobilization, Gi-mediated modulation of cAMP production, or Gi-mediated phosphorylation of ERK1/2 and Akt.

In some embodiments, the $A_3R$ is partially agonized in a manner biased toward cardioprotective functions of the $A_3R$ receptor via preferential activation of intracellular calcium mobilization with less, or no, activation of other $A_3R$-mediated pathways, or via preferential activation of Gq11-mediated intracellular calcium mobilization, Gi-mediated modulation of cAMP production, or Gi-mediated phosphorylation of ERK1/2 and Akt.

In some embodiments, the method increases neuroprotection or neurorestoration in a patient who is suffering from a neurological side effect associated with or resulting from cancer chemotherapy or brain surgery.

In some embodiments, a solid form of compound A, or a pharmaceutically acceptable composition comprising the same, is administered orally.

In one aspect, the present invention provides a method of increasing neuroprotection or neurorestoration in a patient who has suffered a TBI or stroke, thereby treating the TBI or stroke, comprising administering to a patient in need thereof an effective amount of a solid form of compound A, or a pharmaceutically acceptable composition comprising the same.

In one aspect, the present invention provides a method of increasing cardioprotection or regeneration of damaged heart tissue in a patient who has suffered a cardiac ischemia or myocardial infarction, thereby treating the cardiac ischemia or myocardial infarction, comprising administering to a patient in need thereof an effective amount of a solid form of compound A, or a pharmaceutically acceptable composition comprising the same.

In some embodiments, the recovery period after the TBI, stroke, cardiac ischemia, or myocardial infarction is decreased as compared with an untreated patient.

In some embodiments, the $A_3R$ is partially agonized in a manner biased toward neuroprotective functions of the $A_3R$ receptor.

In some embodiments, the $A_3R$ is partially agonized in a manner biased toward cardioprotective functions of the $A_3R$ receptor.

In some embodiments, a solid form of compound A, or a pharmaceutically acceptable composition comprising the same, is administered orally.

In some embodiments, the compound is a biased agonist of an $A_3R$ with improved cardioprotection function relative to a full $A_3R$ agonist.

In some embodiments, a solid form of compound A, or a pharmaceutically acceptable composition comprising the same, is a biased agonist of an $A_3R$ with improved cardioprotection function relative to a full $A_3R$ agonist via preferential activation of one or more of the following A₃R-mediated pathways: activation of Gq11-mediated intracellular calcium mobilization, Gi-mediated modulation of cAMP production, Gi-mediated phosphorylation of ERK1/2 and Akt, or modulation of Beta-Arrestin activation.

In some embodiments, a solid form of compound A, or a pharmaceutically acceptable composition comprising the same, is a biased agonist of an A₃R with improved cardioprotection function relative to a full A₃R agonist via preferential activation of intracellular calcium mobilization with less or no activation of the other A₃R-mediated pathways.

In some embodiments, a solid form of compound A, or a pharmaceutically acceptable composition comprising the same, is a partial agonist of the A₃R with improved cardioprotection function relative to a full A₃R agonist.

Addictive Disorders

Disclosed compounds are also useful in treating addictions, addictive behaviors, behavioral addictions, compulsive disorders and behaviors, and related conditions.

The use of compounds such as compound A in treating such addictions, behaviors, and disorders is described in WO/2019/157317, the contents of which are hereby incorporated by reference.

Cocaine self-administering mice exhibit significantly higher glutamate levels in the VTA (ventral tegmental area) of the brain. The VTA, in particular the VTA dopamine neurons, serve several functions in the reward system, motivation, cognition, and drug addiction, and may be the focus of several psychiatric disorders. The elevated glutamate levels appear to be due, at least in part, to loss of glutamate uptake into astrocytes. Without wishing to be bound by theory, it is believed that reduced availability of glutamate has negative effects on astrocyte function and this loss of function affects neuronal activity and drug-seeking behavior. It has now been found that the compounds disclosed herein treat or prevent relapse in addicted individuals, for example by reversing such loss of astrocyte function. Such loss of astrocyte function may be partly due to reduced expression of the glutamate transporter (GLT-1) in astrocytes. Since astrocytes metabolize glutamate to produce ATP, this likely impairs glutamate uptake, weakens astrocyte oxidative metabolism and downstream ATP-dependent processes and thereby weakens their ability to maintain an optimal environment for VTA neuronal activity.

Accordingly, in one aspect, the present invention provides a method of preventing, ameliorating, treating, or promoting recovery from an addiction, addictive behavior, behavioral addiction, brain reward system disorder, compulsive disorder, or related condition, comprising administering to a subject in need thereof an effective amount of a solid form of compound A, or a pharmaceutically acceptable composition comprising the same.

In some embodiments, the addiction is to an addictive substance. In some embodiments, the addictive substance is a prescription or recreational drug.

In some embodiments, the addictive substance is selected from alcohol, nicotine, a stimulant, a cannabinoid agonist, or an opioid agonist. In some embodiments, the addictive substance is selected from heroin, cocaine, alcohol, an inhalant, an opioid, nicotine, an amphetamine, or a synthetic analog, salt, composition, or combination thereof.

In some embodiments, the amphetamine is selected from bupropion, cathinone, MDMA, or methamphetamine.

In some embodiments, the prescription or recreational drug is selected from a cannabinoid agonist or opioid agonist.

In some embodiments, the addiction is an alcohol or nicotine addiction.

In some embodiments, the subject is a polydrug abuser.

In some embodiments, the prescription or recreational drug is selected from cocaine, heroin, bupropion, cathinone, MDMA, or methamphetamine morphine, oxycodone, hydromorphone, fentanyl, or a combination thereof.

In some embodiments, a disclosed compound increases energy metabolism mediated by astrocytes, such as astrocyte mitochondria. In some embodiments, the compound reverses loss of glutamate uptake into astrocytes caused by a substance with abuse potential. In some embodiments, the compound at least partially reverses the remodeling of the brain reward system caused by the addiction. In some embodiments, such effects are mediated by brain or CNS adenosine A₃ receptors, such as astrocyte A₃R in the VTA; or microglia A₃R.

In another aspect, the present invention provides a method of preventing, ameliorating, treating, or promoting recovery from an addiction, addictive behavior, behavioral addiction brain reward system disorder, compulsive disorder, or related condition by increasing energy metabolism mediated by astrocytes, glia, microglia, neurons, endothelium cells, or other cells of the brain and/or CNS, comprising administering to a subject in need thereof an effective amount of a solid form of compound A, or a pharmaceutically acceptable composition comprising the same.

In some embodiments, the method treats or prevents a relapse of an addiction or addictive behavior in the subject. In some embodiments, the subject is addicted to one or more addictive substances such as addictive drugs (drugs having abuse potential). As described below, such drugs include prescription drugs and recreational drugs such as heroin, cocaine, nicotine, or an opioid agonist.

In another aspect, the present invention provides a method of treating or preventing withdrawal caused by addiction to one or more addictive substances or drugs, comprising administering to a subject in need thereof an effective amount of a solid form of compound A, or a pharmaceutically acceptable composition comprising the same. In some embodiments, the compound decreases withdrawal symptoms in an addicted individual in withdrawal. In some embodiments, the compound treats withdrawal in an addicted individual in withdrawal. In some embodiments, the method further comprises co-administering another drug for treating withdrawal and, optionally, counseling such as psychotherapy. In some embodiments, the method further comprises a cognitive behavioral therapy. In some embodiments, the method further comprises a digital therapeutic. Digital therapeutics include, for example, reSET or reSET-O (Pear Therapeutics).

In some embodiments, the present invention provides a method of treating or preventing a relapse of a compulsive disorder or compulsive behavior, comprising administering to a subject in need thereof an effective amount of a solid form of compound A, or a pharmaceutically acceptable composition comprising the same.

In some embodiments, the compulsive disorder is obsessive-compulsive disorder (OCD), Tourette syndrome, trichotillomania, anorexia, bulimia, anxiety disorder, psychosis, or post-traumatic stress disorder.

According to another aspect, the present invention provides a method for treating one or more behavioral addictions and addictive behaviors or disorders comprising administering to a subject in need thereof a solid form of compound A, or a pharmaceutically acceptable composition comprising the same. Behavioral addictions and addictive disorders result from the intoxication one senses from the release of brain chemicals (e.g., serotonin, adrenaline, epinephrine, etc.) during certain activities. Such disorders are known in the art and include gambling, sex addiction, pornography addiction, eating disorders, spending addiction, rage/anger, workaholism, exercise addiction, risk taking addictions (e.g. kleptomania and pyromania), perfectionism, internet or video game addiction, and compulsive use of electronic devices such as texting and checking social media, to name a few.

In some embodiments, activation of astrocytes is achieved through contacting with a disclosed compound one or more purinergic receptors such as adenosine receptors (ARs), for example those associated with or expressed by astrocytes or microglia, thus modulating the activity of the one or more receptors. In some embodiments, through effects on adenosine receptors such as $A_1$, $A_{2A}$, $A_{2B}$ and $A_3$ on astrocytes, the compound activates astrocytes to treat one or more disclosed diseases or conditions. In some embodiments, after administration to a subject in need thereof, a disclosed compound influences one or more functions such as glutamate uptake having an impact on energy metabolism of astrocytes or neuronal function, thus treating one or more diseases or conditions. In some embodiments, the compound is an AR agonist. In some embodiments, the purinergic receptor is an adenosine $A_3$ receptor ($A_3R$). In some embodiments, the compound is an $A_3R$ agonist. In some embodiments, the compound is a partial agonist or biased agonist or biased partial agonist, at an $A_3$ receptor ($A_3R$), such as a human $A_3$ receptor (hA3R). In some embodiments, the compound is a biased antagonist at an $A_3$ receptor. In some embodiments, the compound acts by dual agonism at an $A_3R$ and an $A_1R$. In some embodiments, the compound is a solid form of compound A, or a pharmaceutically acceptable composition comprising the same.

P2Y receptors are G-protein-coupled receptors and different subtypes of these receptors have important roles in processes such as synaptic communication, cellular differentiation, ion flux, vasodilation, blood brain barrier permeability, platelet aggregation and neuromodulation. Characterized members of the purinergic P2Y receptor family include the mammalian $P2Y_1$, $P2Y_{11}$, $P2Y_{12}$ and $P2Y_{13}$ receptors, which bind to adenine nucleotides; the $P2Y_4$, $P2Y_6$, and $P2Y_{14}$ receptors, that bind to uracil nucleotides; and the $P2Y_2$ and rodent $P2Y_4$ receptors, which have mixed selectivity. In some embodiments, activation of astrocytes is achieved through contacting with a disclosed compound one or more purinergic receptors such as P2Y receptors, for example those associated with or expressed by astrocytes, thus modulating the activity of the one or more receptors. In some embodiments, through effects on P2Y receptors such as $P2Y_1$, $P2Y_{11}$, $P2Y_{12}$ and $P2Y_{13}$ receptors associated with or expressed by astrocytes, the compound activates astrocytes to treat one or more disclosed diseases or conditions. In some embodiments, the P2Y receptor is a $P2Y_1$ receptor. In some embodiments, the $P2Y_1$ receptor is located on intracellular mitochondrial membranes. In some embodiments, the compound is a P2Y agonist. In some embodiments, the compound is a $P2Y_1$ agonist, e.g. at a human $P2Y_1$ receptor. In some embodiments, the compound is a biased agonist, partial agonist, or biased partial agonist at a $P2Y_1$ receptor, such as a human $P2Y_1$ receptor. In some embodiments, the compound is a biased antagonist at a $P2Y_1$ receptor. In some embodiments, the compound is a solid form of compound A, or a pharmaceutically acceptable composition comprising the same.

As used herein, the term "addiction" includes, unless otherwise specified, physical or psychological dependence on a substance. Addiction may involve withdrawal symptoms or mental or physical distress if the substance is withdrawn. Addiction includes drug liking, drug dependence, habit-formation, neurological and/or synaptic changes, development of brain reward system disorders, behavioral changes, or other signs or symptoms of addiction in a subject.

As used herein, the term "addictive drug" or "drug having abuse potential" includes drugs and other substances such as nicotine, whether approved by a regulatory body for treatment of a disease or not, that are known to result in clinical, behavioral, or neurological manifestations of addiction or compulsive behavior. In some embodiments, the addictive drug includes nicotine, a cannabinoid agonist, a stimulant, or an opioid agonist. "Addictive substance" refers to addictive drugs as well as other substances of abuse such as alcohol. Examples of addictive substances thus include heroin, cocaine, alcohol, opiates, nicotine, inhalants, amphetamines, and their synthetic analogs.

Pharmaceutically Acceptable Compositions

According to another embodiment, the invention provides a composition comprising a disclosed compound and a pharmaceutically acceptable carrier, adjuvant, or vehicle. In certain embodiments, a composition of this invention is formulated for administration to a patient in need of such composition. In some embodiments, a composition of this invention is formulated for oral administration to a patient.

The term "biological sample," as used herein, includes, without limitation, cell cultures or extracts thereof; biopsied material obtained from a mammal or extracts thereof; and blood, saliva, urine, feces, semen, tears, or other body fluids or extracts thereof.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 0.01 mg/kg to about 25 mg/kg, of subject body weight per day, one or more times a day, to obtain the desired therapeutic effect. In certain embodiments, the compounds of the invention are administered orally or parenterally at dosage levels of about 0.01 mg/kg to about 50 mg/kg, or about 0.01 mg/kg to about 25 mg/kg, or about 0.05 mg/kg to about 10 mg/kg, or about 0.05 mg/kg to about 5 mg/kg, or about 0.1 mg/kg to about 2.5 mg/kg, of subject body weight per day, one or more times a day, to obtain the desired therapeutic effect.

Liquid dosage forms for oral administration include, but are not limited to, pharmaceutically acceptable emulsions, liposomes, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters), poly(anhydrides) and cyclodextrins and modified cyclodextrins (such as SBE-bCD). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention can also be administered topically, such as directly to the eye, e.g., as an eye-drop or ophthalmic ointment. Eye drops typically comprise an effective amount of at least one compound of the invention and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, 1985, Trans Ophthalmol Soc U K 104(Pt 4): 402-9; Ashton et al., 1991, J Pharmacol Exp Ther 259(2): 719-24; Green et al., 1971, Am J Ophthalmol 72(5): 897-905). The most commonly used penetration enhancer is benzalkonium chloride (Tang et al., 1994, J Pharm Sci 83(1): 85-90; Burstein et al, 1980, Invest Ophthalmol Vis Sci 19(3): 308-13), which also works as preservative against microbial contamination. It is typically added to a final concentration of 0.01-0.05%.

Combinations with Other Therapeutic Agents

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In certain embodiments, a provided compound, or composition thereof, is administered in combination with other therapeutic agents, such as tissue plasminogen activators, blood thinners, statins, ACE inhibitors, angiotensin II receptor blockers (ARBs), beta blockers, calcium channel blockers or diuretics, to a patient in need thereof.

In certain embodiments, the tissue plasminogen activator used in combination with compounds or compositions of the invention include, but are not limited to, alteplase, desmoteplase, reteplase, tenecteplase, or combinations of any of the above.

In certain embodiments, the blood thinners used in combination with compounds or compositions of the invention include, but are not limited to, warfarin, heparin, apixabam, clopidogrel, aspirin, rivaroxaban, dabigatran, or combinations of any of the above.

In certain embodiments, the statins used in combination with compounds or compositions of the invention include, but are not limited to, atorvastatin, rosuvastatin, fluvastatin, lovastatin, pravastatin, simvastatin and pitavastatin, cerivastatin, mevastatin, or combinations of any of the above.

In certain embodiments, the ACE inhibitors used in combination with compounds or compositions of the invention include, but are not limited to, captopril, enalapril, fosinopril, lisinopril, moexipril, perindopril, quinapril, ramipril, trandolapril benazepril, or combinations of any of the above.

In certain embodiments, the angiotensin II receptor blockers (ARBs) used in combination with compounds or compositions of the invention include, but are not limited to, azilsartan, candesartan, eprosartan, irbesartan, losartan, olmesartan, telmisartan, valsartan, fimasartan, or combinations of any of the above.

In certain embodiments, the beta blockers used in combination with compounds or compositions of the invention include, but are not limited to, atenolol, bisoprolol, betaxolol, carteolol, carvedilol, labetalol, metoprolol, nadolol, nebivolol, oxprenolol, penbutolol, pindolol, propranolol, timolol, or combinations of any of the above.

In certain embodiments, the calcium channel blockers used in combination with compounds or compositions of the invention include, but are not limited to, dihydropyridines: amlodipine, cilnidipine, clevidipine, felodipine, isradipine, lercanidipine, levamlodipine, nicardipine, nifedipine, nimodipine, nisoldipine, nitrendipine, diltiazem, verapamil, or combinations of any of the above.

In certain embodiments, the diuretics used in combination with compounds or compositions of the invention include, but are not limited to, loop diuretics, thiazide diuretics, thiazide-like diuretics and potassium-sparing diuretics, or combinations of any of the above.

In certain embodiments, the loop diuretics used in combination with compounds or compositions of the invention include, but are not limited to, bumetanide, ethacrynic acid, furosemide, torsemide, or combinations of any of the above.

In certain embodiments, the thiazide diuretics used in combination with compounds or compositions of the invention include, but are not limited to, epitizide, hydrochlorothiazide and chlorothiazide, bendroflumethiazide, methyclothiazide, polythiazide, or combinations of any of the above.

In certain embodiments, the thiazide-like diuretics used in combination with compounds or compositions of the invention include, but are not limited to, indapamide, chlorthalidone, metolazone, or combinations of any of the above.

In certain embodiments, the potassium-sparing diuretics used in combination with compounds or compositions of the invention include, but are not limited to, amiloride, triamterene, spironolactone, eplerenone, or combinations of any of the above.

In certain embodiments, a provided compound, or composition thereof, is administered in combination with a mechanical thrombectomy device, to a patient in need thereof. In certain embodiments, the mechanical thrombectomy device is a stroke thrombectomy device or a coil embolization device for cerebral aneurysm. In certain embodiments, such a device includes, but is not limited to, a coil retriever, an aspiration device or a stent retriever.

In certain embodiments, a combination of 2 or more therapeutic agents may be administered together with compounds or compositions of the invention. In certain embodiments, a combination of 3 or more therapeutic agents may be administered together with compounds or compositions of the invention.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the present invention, an additional therapeutic agent, and a pharmaceutically acceptable carrier, adjuvant, or vehicle.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between about 0.001-100 mg/kg body weight/day of the additional therapeutic agent can be administered, or about 0.001 mg/kg to about 500 μg/kg, or about 0.005 mg/kg to about 250 μg/kg, or about 0.01 mg/kg to about 100 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of the present invention and one or more additional therapeutic agents. The therapeutic agent may be administered together with a compound of the present invention, or may be administered prior to or following administration of a compound of the present invention. Suitable therapeutic agents are described in further detail below. In certain embodiments, a compound of the present invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of the present invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In some embodiments, the present invention provides a medicament comprising at least one compound of the present invention or a pharmaceutically acceptable salt thereof and a pharmaceutically acceptable carrier.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedures

X-ray powder diffraction (XRPD) analysis was carried out on a Rigaku Smart-Lab X-ray diffraction system. The Rigaku Smart-Lab X-ray diffraction system was configured for reflection Bragg-Brentano geometry using a line source X-ray beam. The x-ray source is a Cu Long Fine Focus tube that was operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1°2θ or less. The axial divergence of the X-ray beam is controlled by 5.0-degree Soller slits in both the incident and diffracted beam paths. The instrument is qualified using ASTM silicon standard on the same day of the analysis.

Powder samples were prepared in a low background Si holder using light manual pressure to keep the sample surfaces flat and level with the reference surface of the sample holder. Each sample was analyzed from 2 to 40°2θ using a continuous scan of 6°2θ per minute with an effective step size of 0.02°2θ.

Thermogravimetric Analysis (TGA) was carried out using a TA Instruments Q50 instrument. The instrument balance was calibrated using class M weights and the temperature calibration was performed using alumel. The nitrogen purge was ~40 mL per minute at the balance and ~60 mL per minute at the furnace. Each sample (about 2-5 mg) was placed into a pre-tared platinum pan and heated from 20° C. to 350° C. at a rate of 10° C. per minute. The heating rate can impact the outcome of the analysis results. Nitrogen purge rate can be varied as appropriate for the specific instrument specifications.

Differential Scanning calorimetry (DSC) analyses were carried out using a TA Instruments Q2000 instrument. The instrument temperature calibration was performed using indium. The DSC cell was kept under a nitrogen purge of ~50 mL per minute during each analysis. The sample (about 1-2 mg) was placed in a standard, crimped, aluminum pan and was heated from 25° C. to 350° C. at a rate of 10° C. per minute. The type of pan, preparation of the pan for analysis, and heating rate can impact the outcome of the analysis results. Nitrogen purge rate can be varied as appropriate for the specific instrument specifications.

Dynamic Vapour Sorption (DVS) analysis was carried out using a TA Instruments Q5000 Dynamic Vapor Sorption analyzer. The instrument was calibrated with standard weights and a sodium bromide standard for humidity. Approximately 20 mg of sample was loaded into a metal-coated quartz pan for analysis. The sample was analyzed at 25° C. with a maximum equilibration time of one hour in 10% relative humidity (RH) steps from 5 to 95% RH (adsorption cycle) and from 95 to 5% RH (desorption cycle). The movement from one step to the next occurred either after satisfying the equilibrium criterion of 0.01% weight change or, if the equilibrium criterion was not met, after one hour. The percent weight change values were calculated using Microsoft Excel®. The temperature for the DVS analysis can impact the outcome of the results.

Karl Fischer (KF) analysis were carried out using a Mettler-Toledo C20 Coulometric KF titrator. The instrument was calibrated using a Hydranal water standard containing 1% water. The titrant was a Hydranal methanol solution. The sample was analyzed in triplicate.

Optical Microscopy (OM) analysis were carried out on a Leica DM 2500 P compound microscope with a 10× magnification eye piece and a 10× magnification objective, for a total magnification of 100×. Images were captured using a QImaging MicroPublisher 3.3 RTV camera. The polarizing microscopy image (in color) was obtained with the sample in mineral oil, with transmitted light from the microscope and polarizers in place.

Infrared (IR) Spectra were obtained using a Thermo Nicolet model 6700 Fourier-transform (FT) IR spectrophotometer equipped with a deuterated triglycine sulfate (DTGS) detector, a potassium bromide (KBr) beamsplitter, and an electronically temperature controlled (ETC) Ever-Gb® IR source. The instrument was configured with a SMART iTR diamond attenuated total reflectance (ATR) sampling accessory. The single beam scan of the background (air) and sample were collected with 128 signal-averaged scans at a resolution of 2 $cm^{-1}$ over the spectral range 4000-400 $cm^{-1}$. The final sample spectrum was automatically calculated and presented in Log 1/R units. The wavelength calibration was verified using a certified polystyrene standard. Data collection and processing was performed using Omnic 9.7.46 software.

FT-Raman Spectra were acquired on a Nicolet model 6700 spectrometer interfaced to a Nexus Raman accessory module. This instrument is configured with a Nd:YAG laser operating at 1024 nm, a $CaF_2$ beamsplitter, and a indium gallium arsenide detector. Samples were packed into a 3-inch glass NMR tube for analysis. The FT-Raman spectrum was collected with 256 signal-averaged scans at a resolution of 4 $cm^{-1}$ over the spectral range 3700-100 $cm^{-1}$. Data collection and processing was performed using Omnic 9.7.46 software.

$^{13}C$ Nuclear Magnetic Resonance (NMR) Spectra were obtained by solid-state $^{13}C$ cross polarization magic angle spinning (CPMAS) experiments were carried out on a 363 MHz Tecmag-based spectrometer. Each sample (approximately 200 mg) was packed into a 7-mm zirconia rotor closed with kel-F end caps for subsequent data acquisition. Glycine, set to 176.0 ppm, was used as an external standard. Acquisition and processing parameters used are shown in Table 3 below.

TABLE 3

Acquisition and Processing Parameters for $^{13}C$ NMR.

| Nucleus | $^{13}C$ |
|---|---|
| Temperature (K) | 293 |
| Observe Frequency (MHz) | 91.37 |
| Sweep Width (Hz) | 29762 |
| Dwell Time (μsec) | 33.6 |
| 1H pulse (μsec) | 5 |
| CP time (msec) | 1 |
| Hartmann-Hahn contact time (msec) | 1 |
| Pulse width (μsec) | 1000 |
| Acquisition Time (msec) | 34 |
| Recycle Delay (sec) | 20 |
| Spin Speed (kHz) | 7.0 |
| Number of Scans | 176 |
| Processing Parameters | |
| Reference | external |
| Line Broadening (Hz) | 15 |

Milling was performed using a Retsch Mill. About 20 mg of material was placed into a plastic grinding cup followed by 10 μL of water and a stainless-steel ball. The sample was then milled at 100% power for 20 minutes.

Example A—General Preparation of Compound A
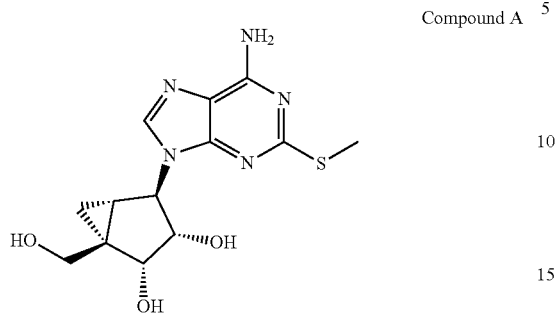
Compound A
The title compound was prepared according to the steps and intermediates (e.g., Scheme 1 and Scheme 2) described below and in the '131 patent and '363 publication, the entireties of each of which is incorporated herein by reference.
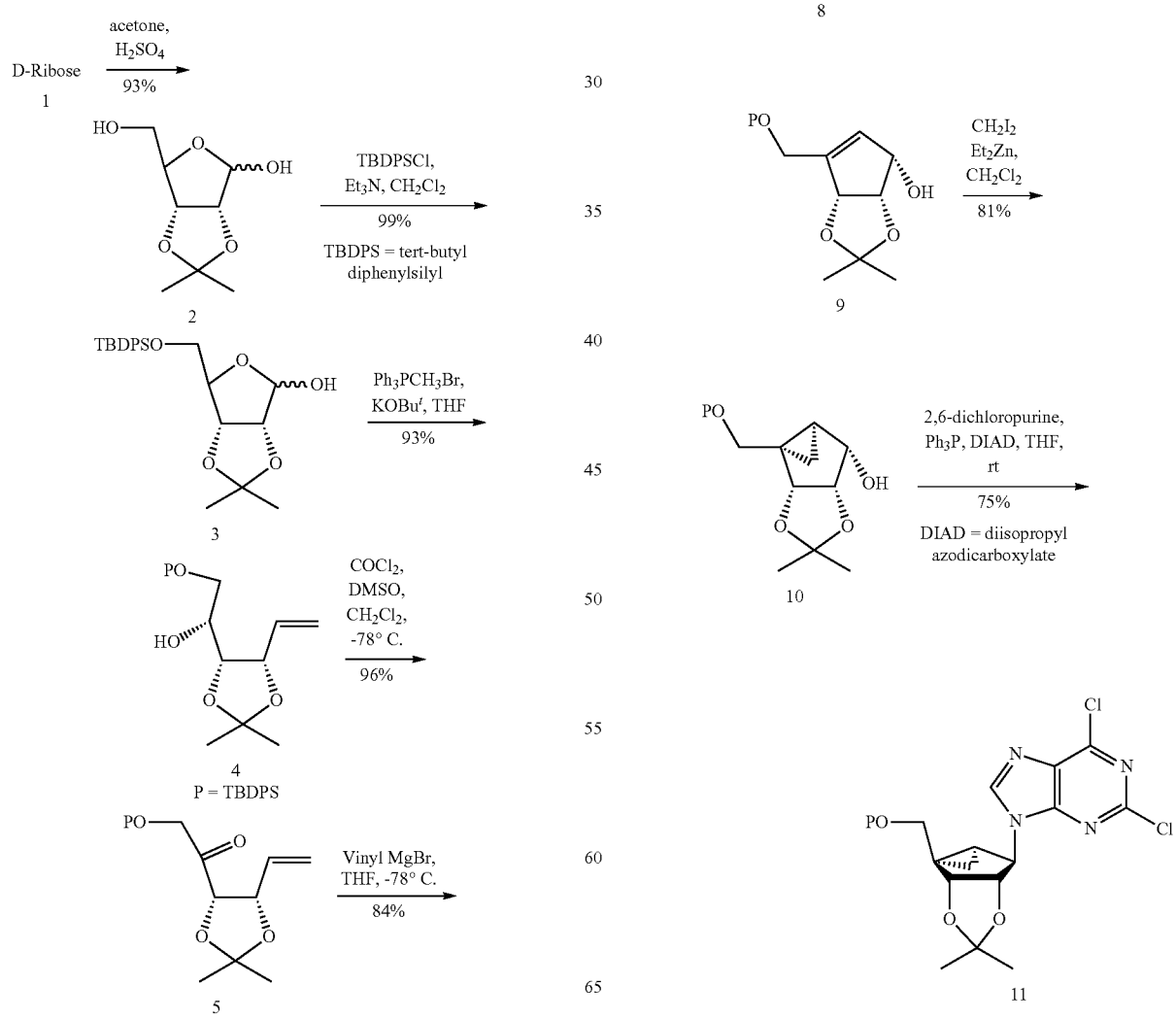

Zhan cat-1B has the following structure:

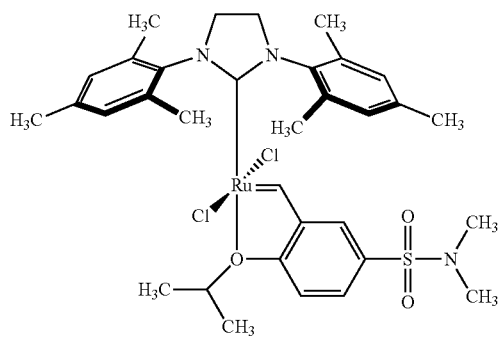

Scheme 2 shows the remainder of the synthesis.

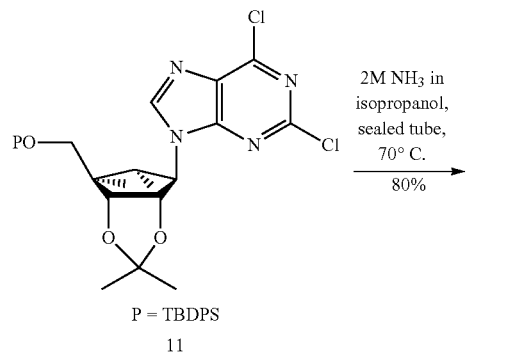

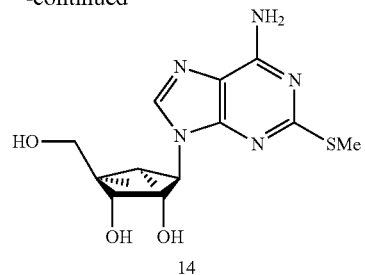

Example 1—Preparation of Free Base Form A of Compound A

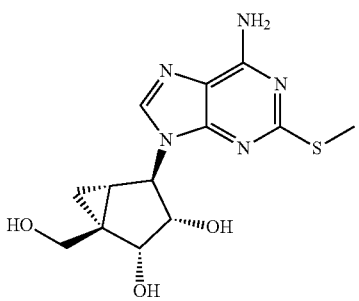

Compound A is prepared according to the methods described in detail in Example 9 of the '131 patent and '363 publication, the entireties of each of which is incorporated herein by reference. Scheme 3 below provides details of the synthesis of Compound A. An intermediate of the synthesis shown in Scheme 3 was used to prepare Form A of Compound A.

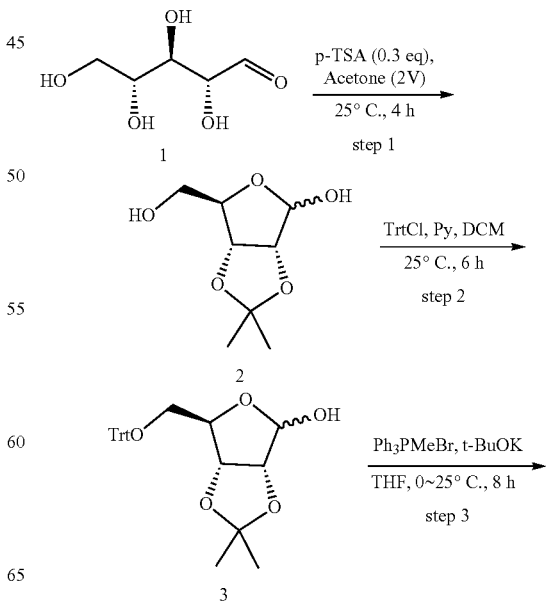

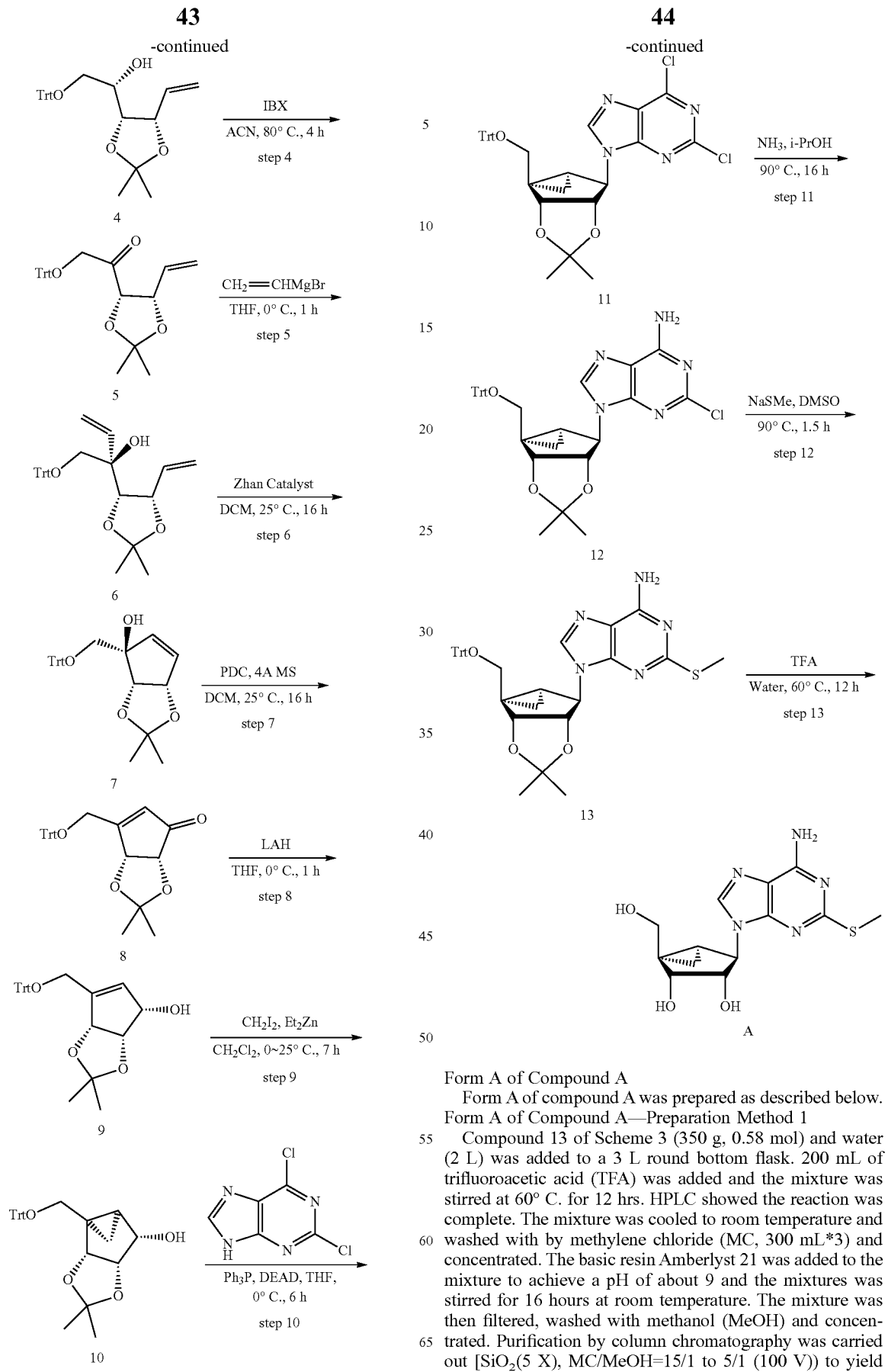

Form A of Compound A

Form A of compound A was prepared as described below.

Form A of Compound A—Preparation Method 1

Compound 13 of Scheme 3 (350 g, 0.58 mol) and water (2 L) was added to a 3 L round bottom flask. 200 mL of trifluoroacetic acid (TFA) was added and the mixture was stirred at 60° C. for 12 hrs. HPLC showed the reaction was complete. The mixture was cooled to room temperature and washed with by methylene chloride (MC, 300 mL*3) and concentrated. The basic resin Amberlyst 21 was added to the mixture to achieve a pH of about 9 and the mixtures was stirred for 16 hours at room temperature. The mixture was then filtered, washed with methanol (MeOH) and concentrated. Purification by column chromatography was carried out [$SiO_2$(5 X), MC/MeOH=15/1 to 5/1 (100 V)) to yield Compound A as light yellow solid. Compound A was then dissolved in HPLC-grade MeOH to a clear solution and rotary evaporated (water pump, bath temperature 35° C.). Form A of compound A was formed gradually during the concentration. After most of the MeOH was removed (no weight change), deionized water was added and rotary evaporated to dryness three times (oil pump, bath temperature 35° C.) to remove residual MeOH. The obtained compound was further dried by rotary evaporation (oil pump, bath temperature 35° C.) until no weight change (~16 hours), yielding Form A of compound A.

Form A of Compound A—Preparation Method 2

To a plastic grinding cup was added 18.4 mg of Compound A and 10 μL of water. A stainless-steel ball was added. The sample was then milled on a Retsch mill at 100% power for 20 minutes at room temperature.

Form A of Compound A—Preparation Method 3

To a 20 mL glass vial was added 200.0 mg of Compound A and 3.0 mL of water. A magnetic stir bar was added and the vial was capped. The vial was placed on a heating/stirring plate and the slurry was stirred magnetically for 7 days at ambient temperature. The vial was centrifuged for 10 minutes and the mother liquor was decanted. A dry air purge was directed into the vial for 10 minutes to dry the solid. The vial was then placed in a room temperature vacuum desiccator for 2 hours.

Form A of Compound A—Preparation Method 4

To a 20 mL glass vial was added 200.0 mg of Compound A and 3.0 mL of water. A magnetic stir bar was added and the vial was capped. The vial was placed on a heating/stirring plate set at 60° C. and the slurry was stirred magnetically for 3 days. The vial was centrifuged for 10 minutes and the mother liquor was decanted. A dry air purge was directed into the vial for 10 minutes to dry the solid. The vial was then placed in a room temperature vacuum desiccator for 2 hours.

Table 1, supra, is reproduced below and sets forth the X-ray diffraction peaks observed for Form A of compound A.

TABLE 1

XRPD Peak Positions for Form A of Compound A.

| °2θ | Relative Intensity | °2θ | Relative Intensity | °2θ | Relative Intensity |
|---|---|---|---|---|---|
| 7.6 | 1.49 | 21.5 | 35.63 | 30.8 | 12.79 |
| 8.0 | 100 | 22.8 | 2.30 | 32.0 | 8.32 |
| 9.0 | 3.49 | 23.1 | 6.16 | 32.8 | 8.27 |
| 10.8 | 4.60 | 23.7 | 4.21 | 32.9 | 13.11 |
| 11.8 | 1.59 | 23.9 | 9.39 | 33.7 | 9.73 |
| 12.5 | 4.59 | 24.9 | 54.39 | 34.7 | 4.31 |
| 13.1 | 59.02 | 26.1 | 32.89 | 36.3 | 3.98 |
| 16.2 | 34.56 | 26.5 | 13.26 | 36.7 | 8.82 |
| 16.7 | 37.68 | 26.6 | 22.22 | 37.9 | 12.68 |
| 17.2 | 10.65 | 27.1 | 60.62 | 38.2 | 3.16 |
| 17.9 | 45.59 | 28.6 | 10.52 | 38.5 | 1.75 |
| 18.1 | 16.05 | 29.3 | 1.66 | 38.7 | 2.83 |
| 18.3 | 10.91 | 29.7 | 9.05 | 39.6 | 2.37 |
| 19.8 | 4.96 | 30.1 | 1.89 | — | — |
| 21.0 | 30.62 | 30.4 | 1.77 | — | — |

Table 4, shown below, sets forth the FT-IR peaks observed for Form A of compound A.

TABLE 4

FT-IR peak listing for Form A of compound A.
Wavenumbers (cm$^{-1}$)

| | | |
|---|---|---|
| 3460 | 1329 | 870 |
| 3293 | 1310 | 828 |
| 3178 | 1245 | 786 |
| 3114 | 1227 | 742 |
| 3008 | 1199 | 680 |
| 2921 | 1129 | 636 |
| 2887 | 1089 | 560 |
| 2871 | 1072 | 545 |
| 1629 | 1054 | 523 |
| 1580 | 1041 | 477 |
| 1510 | 1020 | 450 |
| 1457 | 975 | 418 |
| 1423 | 945 | — |
| 1406 | 886 | — |

Table 5, shown below, sets forth the FT-Raman peaks observed for Form A of compound A.

TABLE 5

FT-Raman peak listing for Form A of compound A.
Raman Shift (cm$^{-1}$)

| | |
|---|---|
| 3085 | 1105 |
| 3052 | 1042 |
| 3009 | 975 |
| 2924 | 895 |
| 2902 | 847 |
| 2873 | 783 |
| 2826 | 742 |
| 1578 | 727 |
| 1512 | 715 |
| 1461 | 703 |
| 1447 | 628 |
| 1424 | 613 |
| 1341 | 564 |
| 1327 | 542 |
| 1251 | — |
| 1223 | — |

Table 6, shown below, sets forth the $^{13}$C NMR peaks observed for Form A of compound A.

TABLE 6

$^{13}$C NMR peak listing for Form A of compound A.
Peak Positions in Parts per Million (ppm)

| |
|---|
| 12.8 |
| 15.0 |
| 20.4 |
| 33.9 |
| 60.4 |
| 66.7 |
| 71.8 |
| 75.4 |
| 116.6 |
| 143.7 |
| 149.6 |
| 154.2 |
| 163.0 |

Table 7, shown below, sets forth selected $^{13}$C NMR peaks and chemical shifts from downfield peaks observed for Form A of compound A.

TABLE 7

13C NMR peaks and chemical shifts for Form A of compound A.

| Peak Positions in Parts per Million (ppm) | Δ (ppm) from the most downfield peak |
|---|---|
| 116.6 | 46 |
| 143.7 | 19 |
| 149.6 | 13 |
| 154.2 | 9 |
| 163.0 | |

FIG. 1 depicts an XRPD pattern of Form A of compound A.

Figure 2:
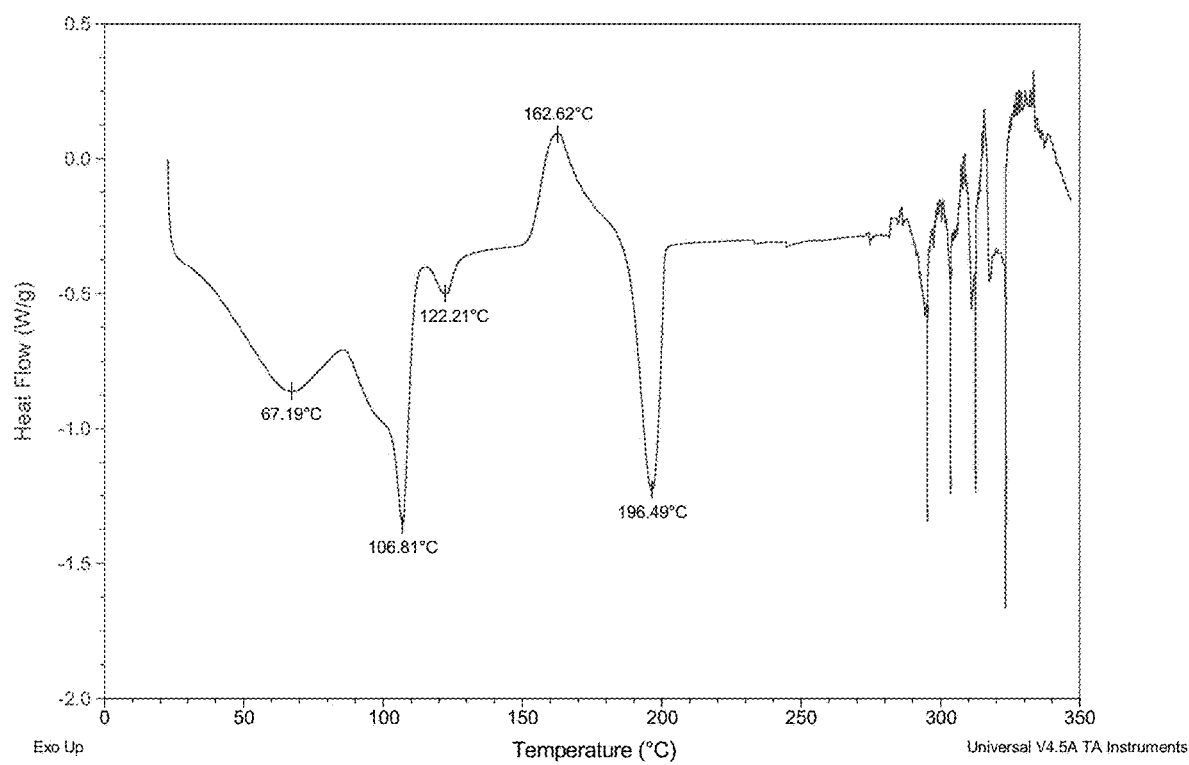
FIG. 2 depicts a DSC trace of Form A of compound A.

FIG. 2 depicts a DSC trace of Form A of compound A.

Figure 3:
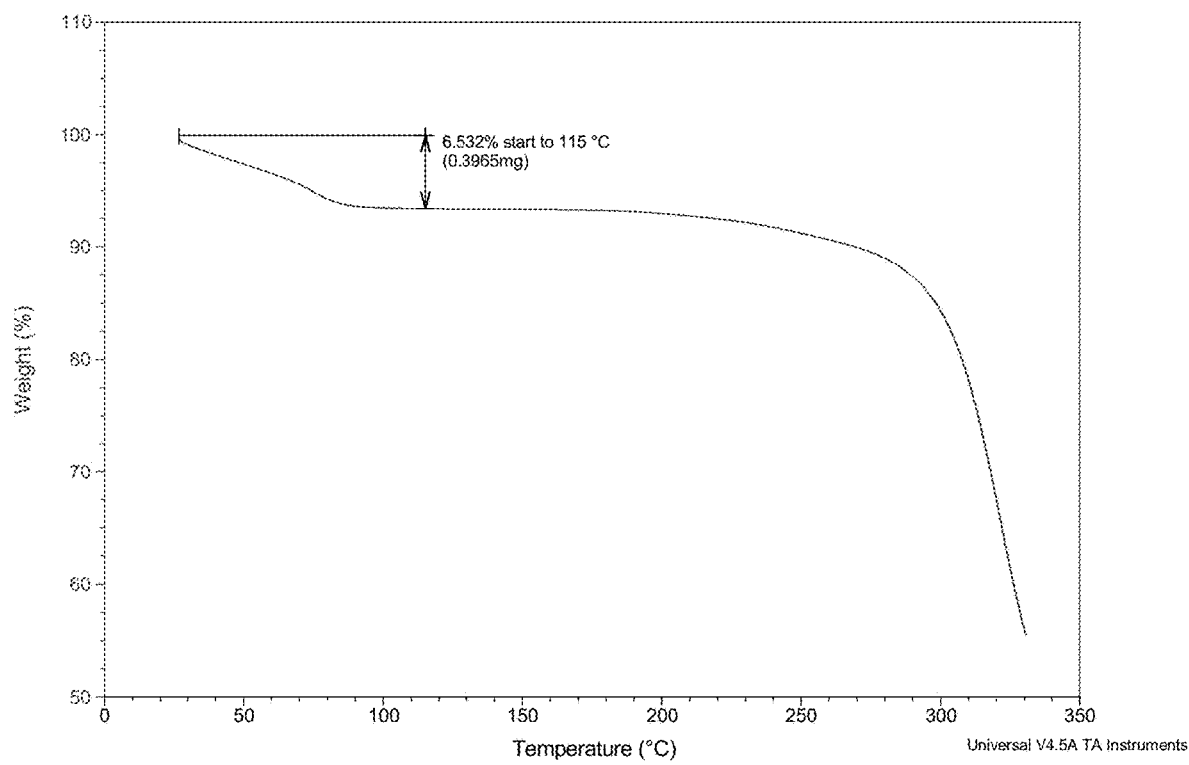
FIG. 3 depicts a TGA trace of Form A of compound A.

FIG. 3 depicts a TGA trace of Form A of compound A.

Figure 4:
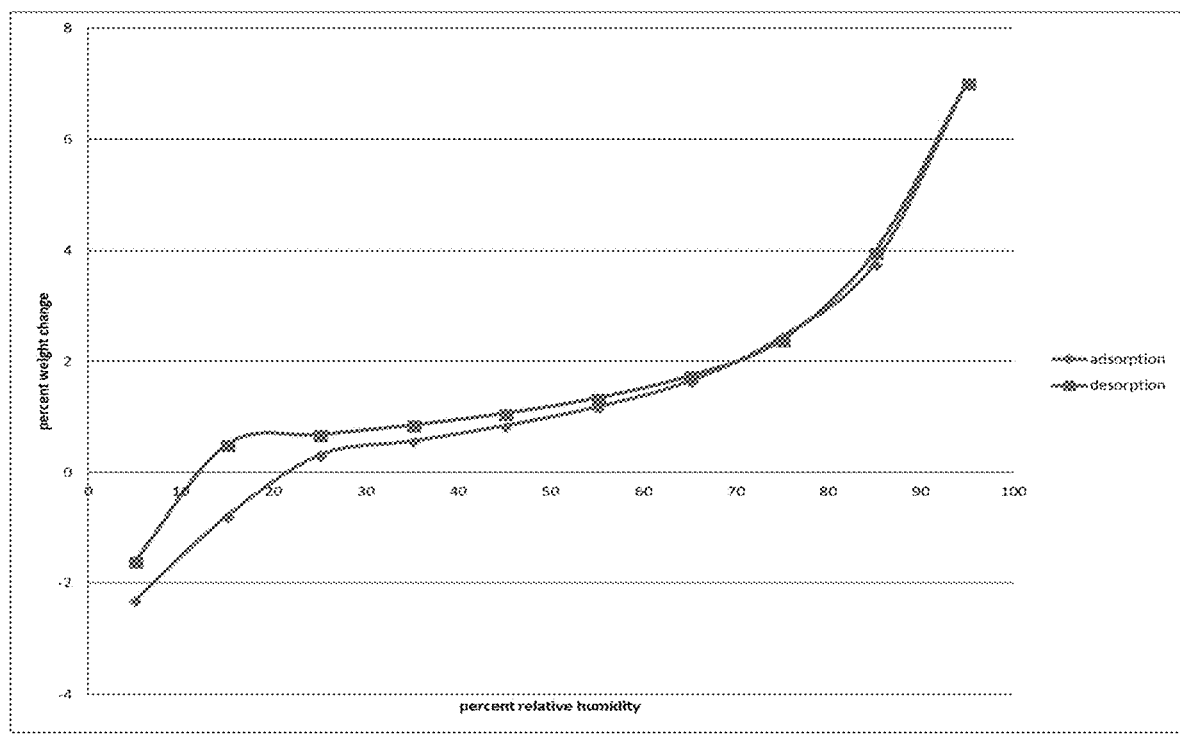
FIG. 4 depicts a DVS trace of Form A of compound A.

FIG. 4 depicts a DVS trace of Form A of compound A.

Figure 5:
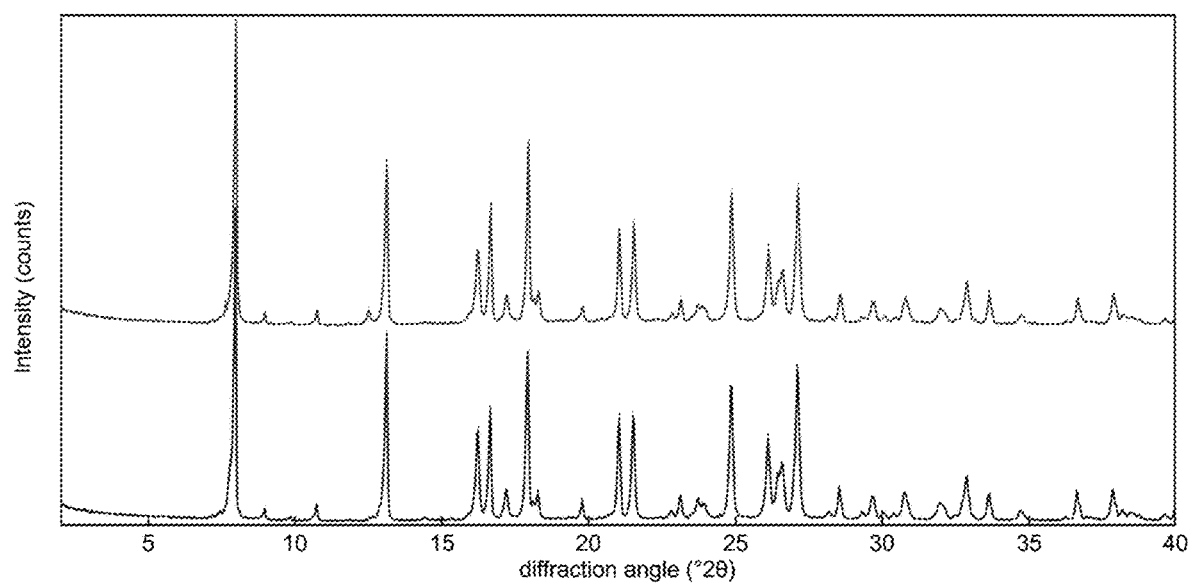
FIG. 5 depicts an XRPD pattern of Form A of compound A before (top) and after (bottom) DVS analysis.

FIG. 5 depicts an XRPD pattern of Form A of compound A before (top) and after (bottom) DVS analysis.

Figure 6:
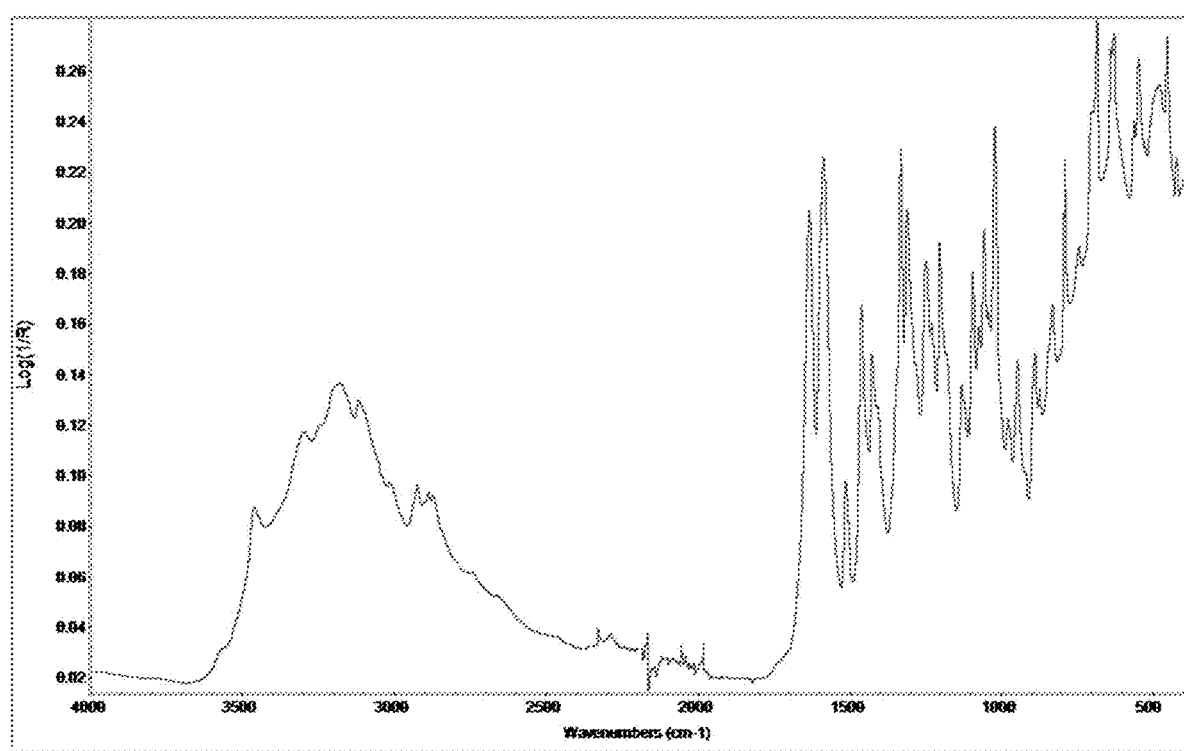
FIG. 6 depicts an FT-IR spectra of Form A of compound A.

FIG. 6 depicts an FT-IR spectra of Form A of compound A.

Figure 7:
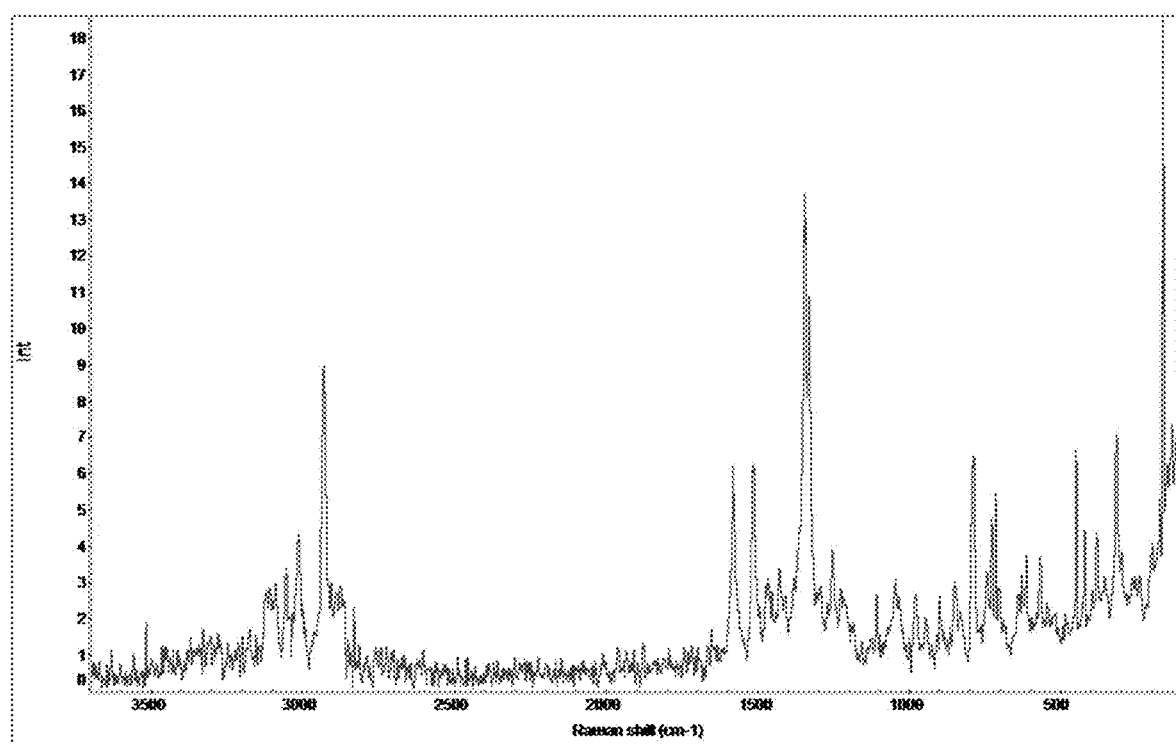
FIG. 7 depicts an FT-Raman spectra of Form A of compound A.

FIG. 7 depicts an FT-Raman spectra of Form A of compound A.

Figure 8:
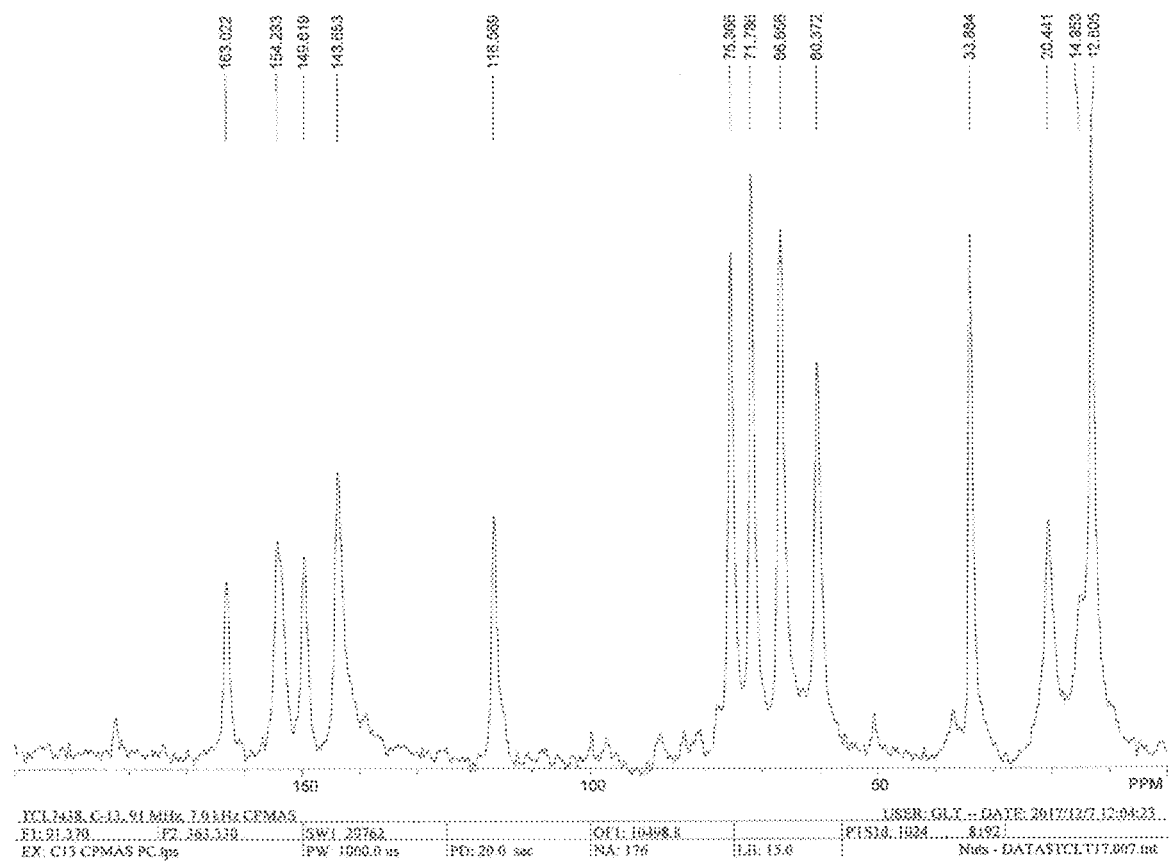
FIG. 8 depicts a solid-state $^{13}$C spectra of Form A of compound A.

FIG. 8 depicts a solid-state 13C spectra of Form A of compound A.

Figure 9:
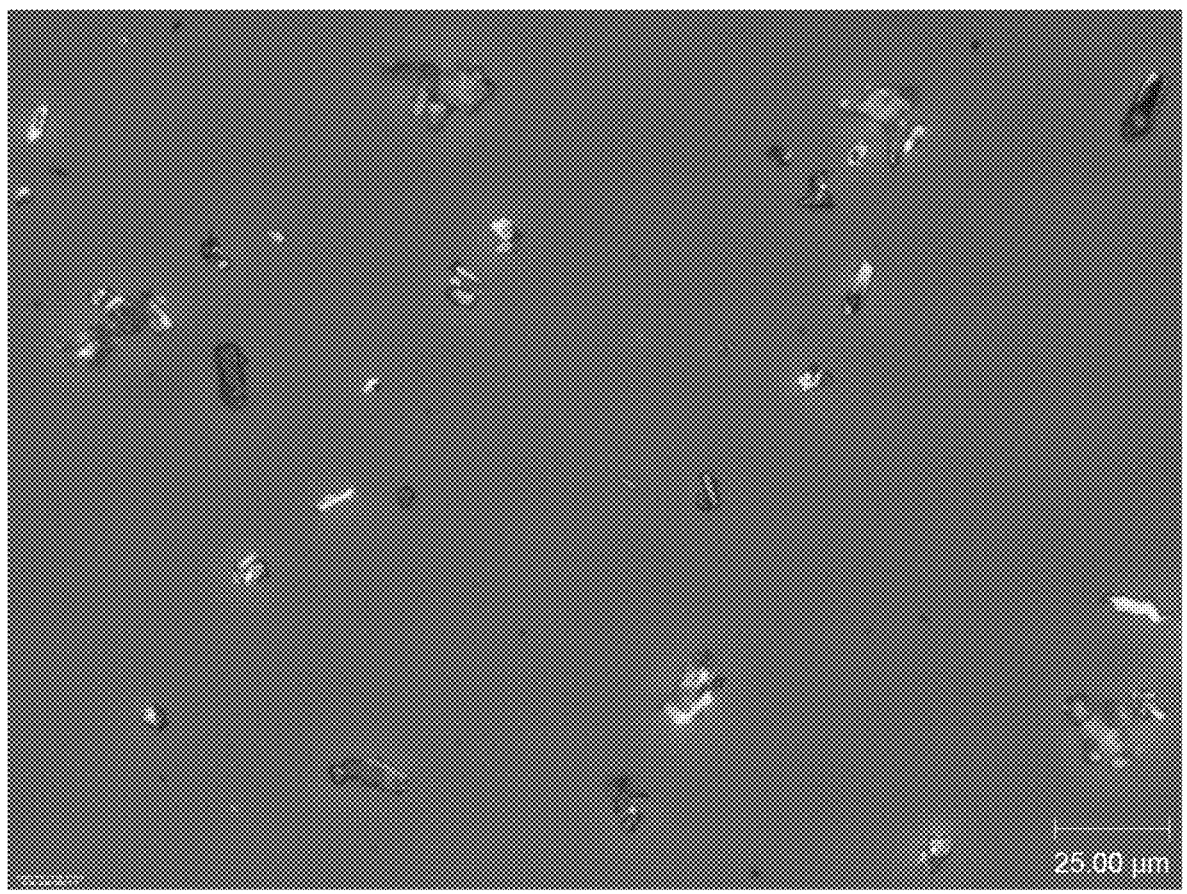
FIG. 9 depicts an optical microscope image of Form A of compound A.

FIG. 9 depicts an optical microscope image of Form A of compound A.

Form A of compound A was observed to have the characteristics described below.

Based on XRPD data, Form A of compound A is crystalline and shows sharp and well resolved x-ray diffraction signals.

Based on optical microscopy images, Form A of compound A shows blade shaped crystals of similar size and shape.

Form A of compound A loses the water of hydration and exhibits a melting point near 196° C. based on the DSC data.

Form A of compound A is hydrated based on TG and KF data, containing between 1.2 and 1.4 moles of water per mole of form A of compound A.

Form A of compound A is stable under various humidity conditions. It is moderately hygroscopic based on the DVS data where approximately 9.3% of moisture gain was observed during the moisture sorption, and about 2% of moisture loss was observed during the desorption cycle. The crystalline form remained unchanged after the DVS analysis where the sample was exposed up to 95% RH (relative humidity), and down to 5% RH.

Form A of compound A is stable when milled in the presence of water or when stirred in water between room temperature and 60° C.

Form A of compound A is more stable than Form B in solvent systems having water activity greater or equal to 0.72. If the solvent system has higher than or equal water activity of 0.72, and the two crystalline forms are mixed, the mixture converts to Form A. The solvent systems can be mixture of any organic solvents and organic solvents containing water.

Form A of compound A has a solid-state 13C NMR spectrum containing single 13C signals for each carbon position in the chemical structure. Therefore, there is one molecule in the asymmetric unit of crystalline form A.

Based on the above, form A of compound A is a moderately hygroscopic, stable, hydrated, crystalline material.

Example 2—Preparation of Free Base Form B of Compound A

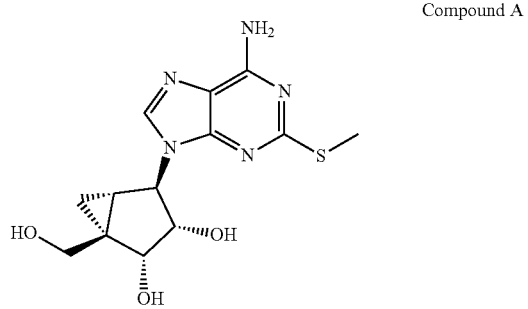 [SMILES: CSc1nc(N)c2ncn([C@H]3[C@H](O)[C@H](O)[C@]4(CO)C[C@H]34)c2n1]

Compound A

Form B of Compound A

Form B of compound A was prepared as described below.

Form B of Compound A—Preparation Method 1

To a 20 mL glass vial was added 200.4 mg of Form A of Compound A and 3.0 mL of acetone. A magnetic stir bar was added and the vial was capped. The vial was placed on a heating/stirring plate set at 60° C. and the slurry was stirred magnetically for 3 days. The vial was centrifuged for 10 minutes and the mother liquor was decanted. A dry air purge was directed into the vial for 10 minutes to dry the solid. The vial was then placed in a room temperature vacuum desiccator for 2 hours.

Form B of Compound A—Preparation Method 2

To a 1-dram glass vial was added 17.2 mg of Form A of Compound A and 1 mL of ethyl acetate. The slurry was stirred magnetically on a heating/stirring plate set to 60° C. and ethanol (absolute) was added until dissolution occurred (added 1 mL). The stir bar was removed, the vial capped, and the heat turned off. Once cooled to ambient temperature, no solid was observed and the vial was left at ambient temperature overnight, during which time crystallization did not occur. The vial was then placed in a refrigerator at about 5° C. and left for 3 days, during which time crystallization did not occur. The vial was then placed in a freezer at about −15° C. and left for 2 days, during which time crystallization occurred. The solid was recovered by filtration.

Form B of Compound A—Preparation Method 3

To a plastic grinding cup was added 18.4 mg of Form A of Compound A and 10 μL of ethanol. A stainless-steel ball was added. The sample was then milled on a Retsch mill at 100% power for 20 minutes.

Form B of Compound A—Preparation Method 4

To a 1-gram glass vial was added 3.8 mg of Form A of Compound A and 0.7 mL of tetrahydrofuran. The solid dissolved. The vial was then placed into a 20 mL glass vial containing 2 mL of hexanes. The 20 mL vial was capped and the sample left at ambient temperature for 6 days, during which crystallization occurred. The solvent was decanted and the solids allowed to air dry.

Table 2, supra, is reproduced below and sets forth the X-ray diffraction peaks observed for Form B of compound A.

TABLE 2

XRPD Peak Positions for Form B of Compound A.

| °2θ | Relative Intensity | °2θ | Relative Intensity | °2θ | Relative Intensity |
|---|---|---|---|---|---|
| 4.7 | 2.43 | 20.1 | 88.35 | 29.5 | 4.27 |
| 7.6 | 3.96 | 21.0 | 42.70 | 29.9 | 3.19 |
| 9.5 | 14.73 | 21.5 | 68.69 | 30.2 | 6.20 |
| 10.0 | 10.55 | 23.0 | 2.13 | 30.6 | 7.95 |
| 10.5 | 7.20 | 23.8 | 53.95 | 31.6 | 4.20 |
| 13.8 | 20.73 | 24.3 | 8.09 | 32.3 | 1.42 |
| 14.2 | 10.53 | 24.6 | 3.80 | 32.7 | 5.03 |
| 14.7 | 40.39 | 25.4 | 5.74 | 33.1 | 4.67 |
| 15.2 | 6.59 | 25.6 | 8.51 | 33.6 | 3.56 |
| 15.4 | 14.70 | 25.9 | 35.31 | 35.9 | 7.11 |
| 16.2 | 4.80 | 26.2 | 20.76 | 37.0 | 2.87 |
| 17.1 | 24.58 | 26.6 | 16.53 | 37.4 | 1.78 |
| 17.9 | 58.03 | 27.6 | 7.29 | 39.0 | 1.26 |
| 18.3 | 12.94 | 28.8 | 25.11 | — | — |
| 19.0 | 100 | 29.1 | 8.40 | — | — |

Table 8, shown below, sets forth the FT-IR peaks observed for Form B of compound A.

TABLE 8

FT-IR peak listing for Form B of compound A.
Wavenumbers (cm⁻¹)

| | | |
|---|---|---|
| 3307 | 1335 | 835 |
| 3248 | 1298 | 791 |
| 3172 | 1239 | 750 |
| 3114 | 1205 | 721 |
| 2898 | 1190 | 694 |
| 2867 | 1171 | 668 |
| 1667 | 1120 | 639 |
| 1589 | 1093 | 613 |
| 1573 | 1074 | 607 |
| 1502 | 1042 | 574 |
| 1443 | 1023 | 553 |
| 1432 | 999 | 499 |
| 1409 | 970 | 436 |
| 1379 | 932 | 427 |
| 1368 | 884 | 418 |
| 1347 | 858 | 401 |

Table 9, shown below, sets forth the FT-Raman peaks observed for Form B of compound A.

TABLE 9

FT-Raman peak listing for Form B of compound A.
Raman Shift (cm⁻¹)

| | |
|---|---|
| 3511 | 997 |
| 3424 | 931 |
| 3115 | 837 |
| 3036 | 788 |
| 2931 | 750 |
| 2900 | 715 |
| 2731 | 669 |
| 1570 | 641 |
| 1502 | 613 |
| 1455 | 546 |
| 1371 | 446 |
| 1337 | 433 |
| 1319 | 446 |
| 1288 | 403 |
| 1248 | 306 |
| 1207 | 183 |
| 1190 | 160 |
| 1039 | — |

Table 10, shown below, sets forth the $^{13}$C NMR peaks observed for Form B of compound A.

TABLE 10

$^{13}$C NMR peak listing for Form B of compound A.
Peak Positions in Parts per Million (ppm)

| |
|---|
| 12.8 |
| 23.2 |
| 36.0 |
| 37.5 |
| 61.9 |
| 63.8 |
| 68.2 |
| 73.9 |
| 76.4 |
| 77.4 |
| 116.7 |
| 136.3 |
| 137.9 |
| 150.4 |
| 155.3 |
| 165.3 |

Table 11, shown below, sets forth selected $^{13}$C NMR peaks and chemical shifts from downfield peaks observed for Form B of compound A.

TABLE 11

$^{13}$C NMR peaks and chemical shifts for Form B of compound A.

| Peak Positions in Parts per Million (ppm) | Δ (ppm) from the most downfield peak |
|---|---|
| 116.7 | 49 |
| 136.3 | 29 |
| 137.9 | 27 |
| 150.4 | 15 |
| 155.3 | 10 |
| 165.3 | |

FIG. 10 depicts an XRPD pattern of Form B of compound A.

Figure 11:
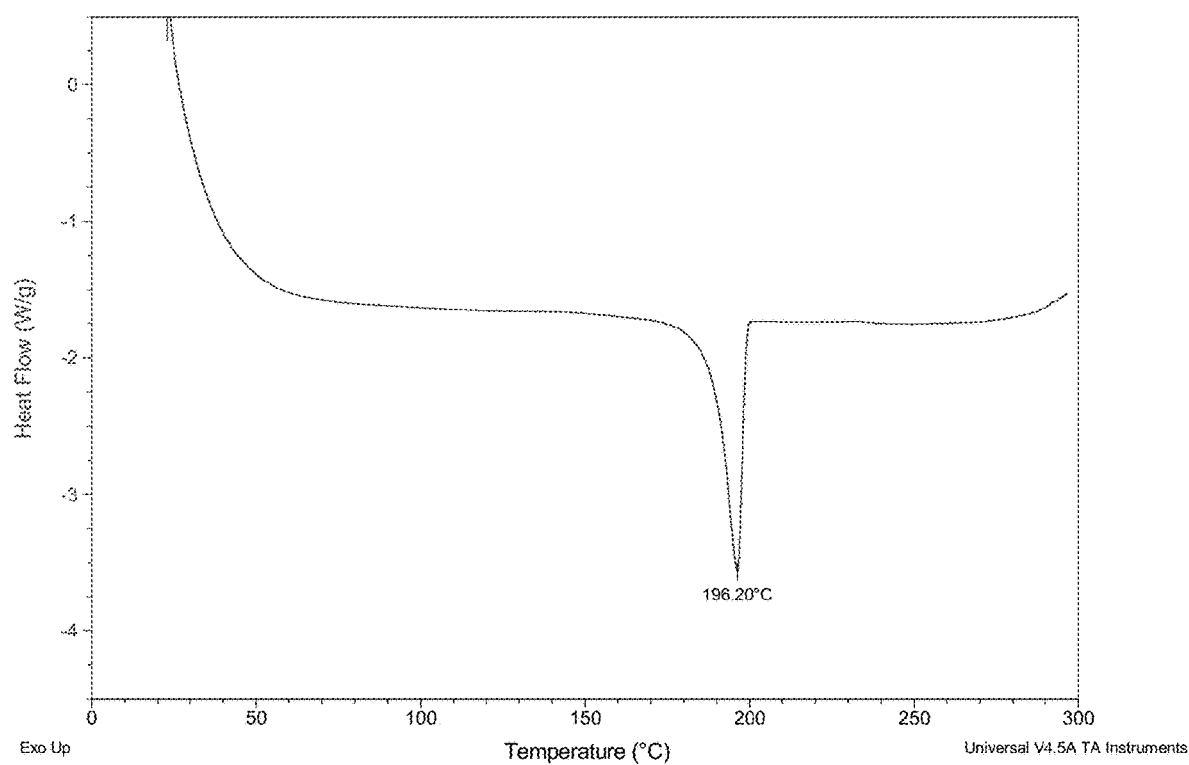
FIG. 11 depicts a DSC trace of Form B of compound A.

FIG. 11 depicts a DSC trace of Form B of compound A.

Figure 12:
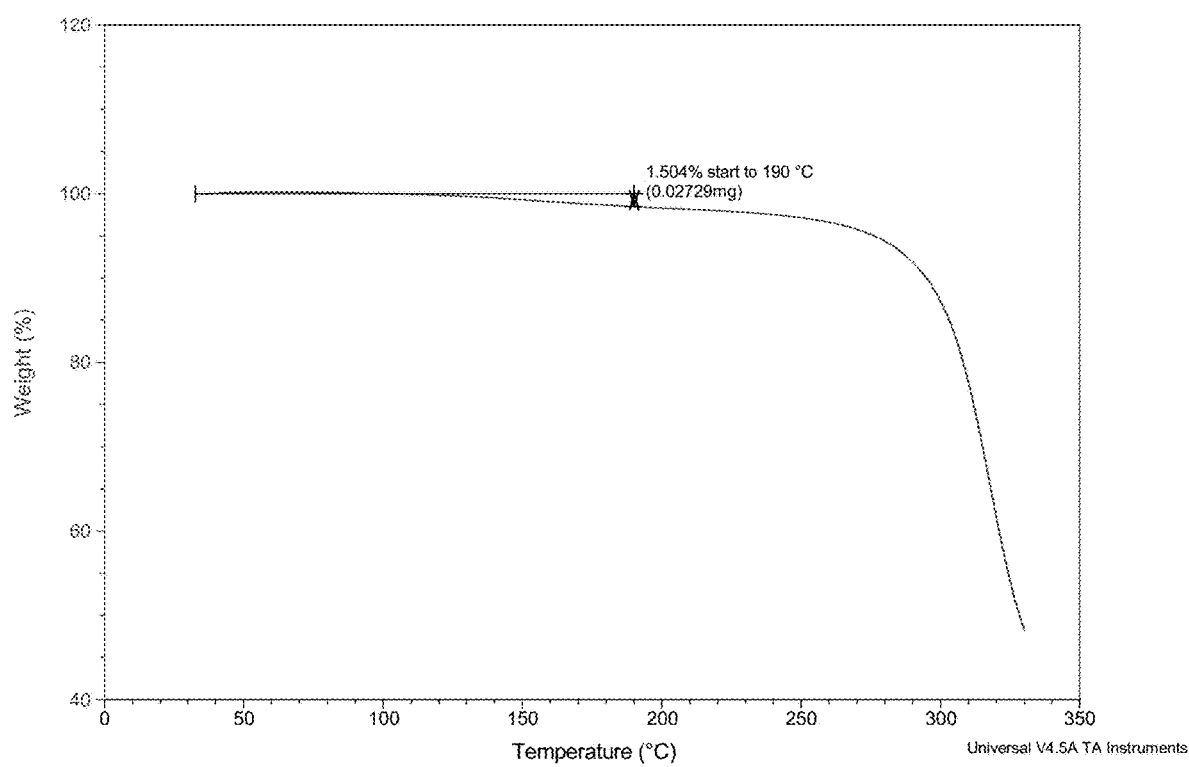
FIG. 12 depicts a TGA trace of Form B of compound A.

FIG. 12 depicts a TGA trace of Form B of compound A.

Figure 13:
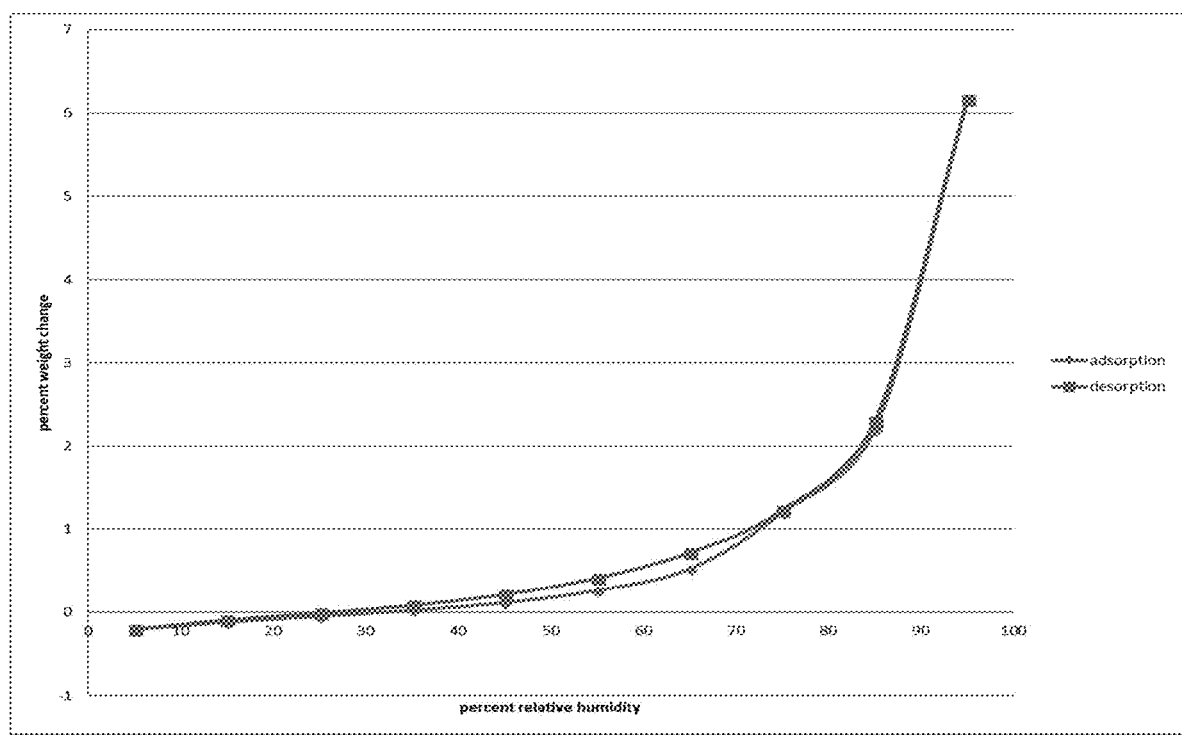
FIG. 13 depicts a DVS trace of Form B of compound A.

FIG. 13 depicts a DVS trace of Form B of compound A.

Figure 14:
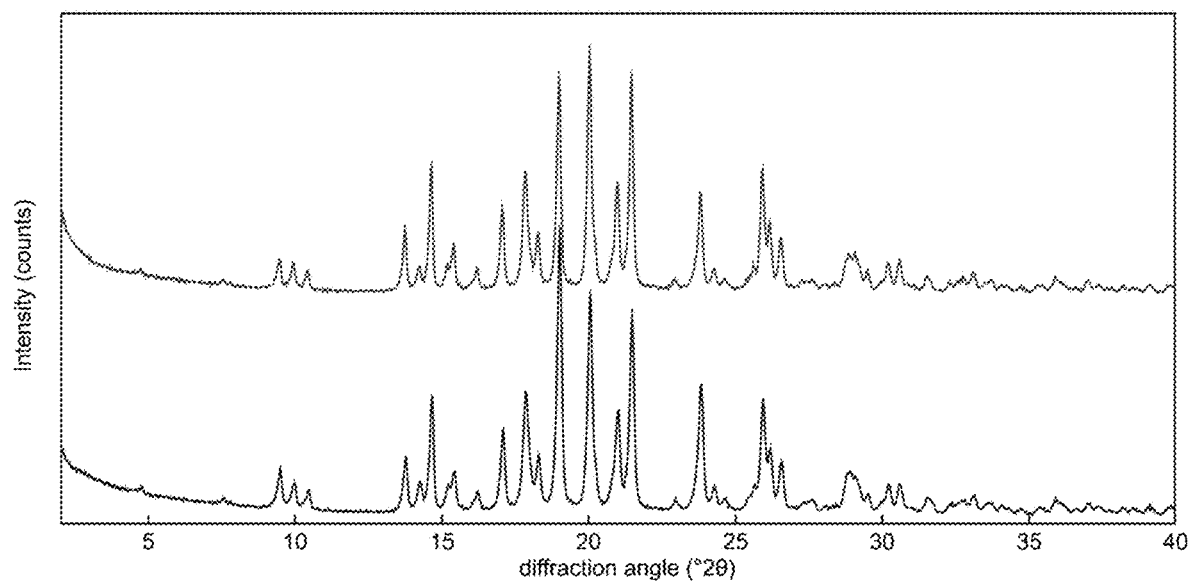
FIG. 14 depicts an XRPD pattern of Form B of compound A before (top) and after (bottom) DVS analysis.

FIG. 14 depicts an XRPD pattern of Form B of compound A before (top) and after (bottom) DVS analysis.

Figure 15:
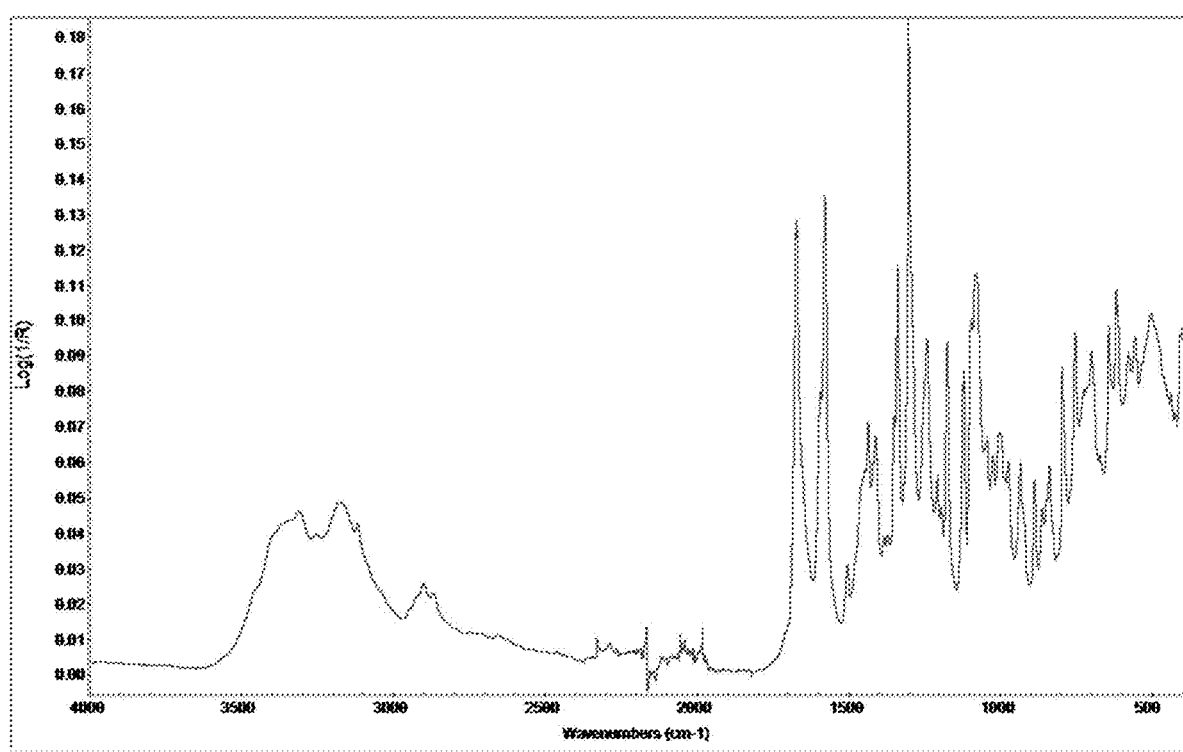
FIG. 15 depicts an FT-IR spectra of Form B of compound A.

FIG. 15 depicts an FT-IR spectra of Form B of compound A.

Figure 16:
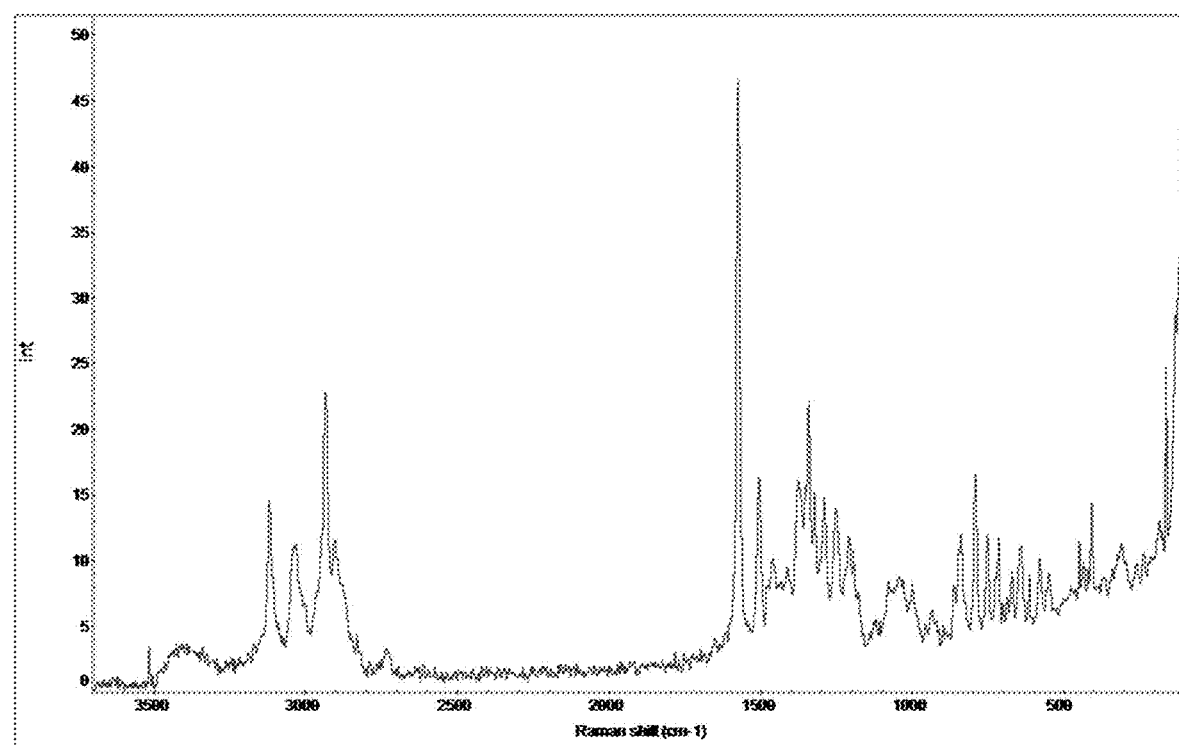
FIG. 16 depicts an FT-Raman spectra of Form B of compound A.

FIG. 16 depicts an FT-Raman spectra of Form B of compound A.

Figure 17:
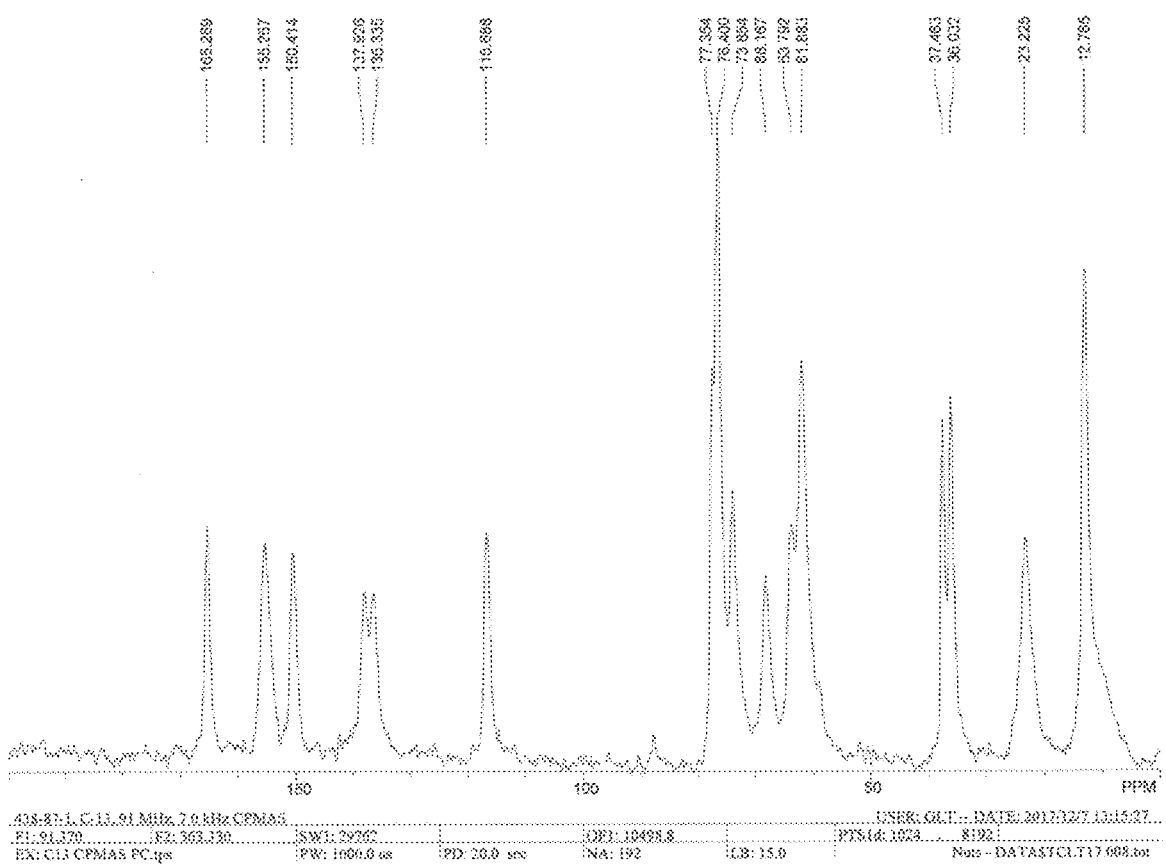
FIG. 17 depicts a solid-state $^{13}$C spectra of Form B of compound A.

FIG. 17 depicts a solid-state $^{13}$C spectra of Form B of compound A.

Figure 18:
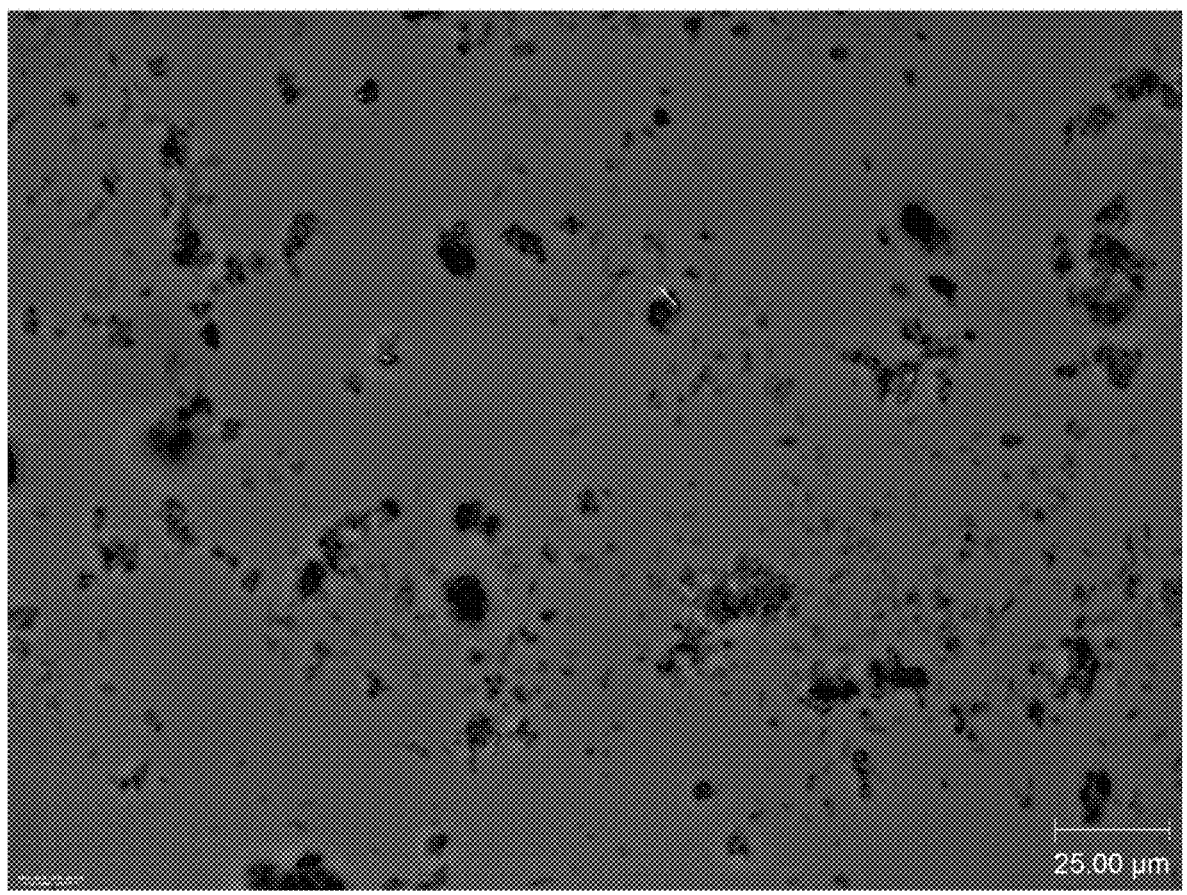
FIG. 18 depicts an optical microscope image of Form B of compound A.

FIG. 18 depicts an optical microscope image of Form B of compound A.

Form B of compound A was observed to have the characteristics described below.

Based on XRPD data, Form B of compound A is crystalline and shows sharp and well resolved x-ray diffraction signals.

Based on optical microscopy images, Form B of compound A shows irregular shaped crystals of similar size and shape.

Form B of compound A exhibits a melting point near 196° C. based on the DSC data.

Form B of compound A is anhydrous and non-solvated based on TG and KF data.

Form B of compound A is moderately hygroscopic based on the DVS data where approximately 6.4% of moisture gain was observed during the moisture sorption. During the desorption cycle, Form B of compound A lost all of the moisture gain. Furthermore, the crystalline form remained unchanged after the DVS analysis where the sample was exposed up to 95% RH and down to 5% RH.

Form B of compound A is more stable than Form A when slurried in organic/water solvent systems having water activity less than or equal to 0.63. The solvent systems can be a mixture of any organic solvents and organic solvents containing water.

Form B of compound A has a solid-state $^{13}$C NMR spectrum containing certain peaks which are clearly doubled. Therefore, there are two conformationally-different molecules in the asymmetric unit of crystalline form B.

Based on the above, form B of compound A is a moderately hygroscopic, stable, unsolvated, anhydrous crystalline material.

Example 3—Single Crystal Studies of Compound A

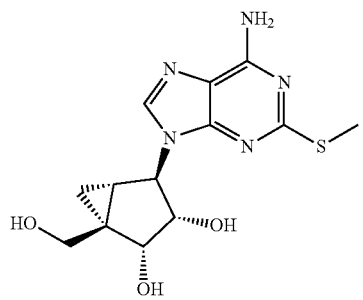

Compound A

Diffraction data for structural determination of compound A will be generated by analysis with an electron cryo-microscope (Cryo-TEM) using the micro-electron-diffraction (microED) technique. MicroED techniques have been described by Jones et al., *ACS Central Science* 2018, 4, 1587-1592; Gruene et al., *Angew. Chem. Int. Ed.* 2018, 57, 16313-16317; and Shi et al., *eLife* 2013, 2, e01345, doi: 10.7554/eLife.01345.

Materials and Methods

Compound A will be prepared according to Example A described above, supra, with no additional crystallization or chemical modification other than crushing, grinding, trituration, milling, or other means of particle size reduction.

To prepare samples of compound A for microED, approximately 1 mg of compound A will be placed between two microscope slides and ground to a fine powder. The ground powder will be placed into an Eppendorf tube along with a TEM grid and shaken. The loaded TEM grid will then be removed from the Eppendorf tube and gently tapped against a filter paper to remove excess powder. Once sample grids of compound A are prepared, they will be subsequently plunged into liquid nitrogen, placed into the sample cartridge, and loaded into the microscope for analysis.

A holey carbon copper grid will be cooled to liquid nitrogen temperatures and transferred to a cryo electron microscope operating at an acceleration voltage of 200 kV (Thermo Fisher Talos Arctica). 140 degrees of diffraction data will be collected from a single nano crystal by continuous rotation at 0.5 degrees per second. An entire data set will be collected as a movie using a bottom mount CetaD CMOS detector fitted with a thick scintillator for diffraction studies. Software written to convert the movie frames into SigmaTel Motion Video (SMV) format will allow for processing in X-ray detector software (XDS).

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A solid form of Compound A:

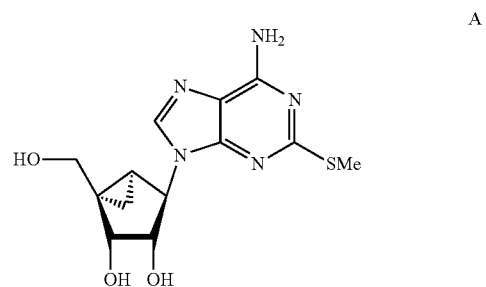

wherein said solid form has one or more peaks in its XRPD selected from those at about 8.0 and about 13.1 degrees 2-theta.

2. The solid form according to claim 1, wherein said solid form is a crystalline solid substantially free of amorphous Compound A.

3. The solid form according to claim 1, wherein said solid form is substantially free of impurities.

4. The solid form according to claim 1, having two peaks in its XRPD selected from those at about 8.0 and about 13.1 degrees 2-theta.

5. The solid form according to claim 1, having an XRPD substantially similar to that depicted in FIG. 1.

6. A pharmaceutical composition comprising the solid form of claim 1 and a pharmaceutically acceptable carrier, excipient, or adjuvant.

7. A solid form of Compound A:

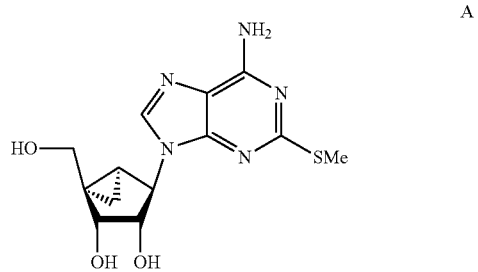

wherein said solid form has one or more peaks in its XRPD selected from those at about 9.5, about 10.5, and about 13.8 degrees 2-theta.

8. The solid form according to claim 7, having at least two peaks in its XRPD selected from those at about 9.5, about 10.5, and about 13.8 degrees 2-theta.

9. The solid form according to claim 7, having an XRPD substantially similar to that depicted in FIG. 10.

10. The solid form according to claim 7, wherein said solid form is a crystalline solid substantially free of amorphous Compound A.

11. The solid form according to claim 7, wherein said solid form is substantially free of impurities.

12. The solid form according to claim 7, having peaks in its XRPD at about 9.5, about 10.5, and about 13.8 degrees 2-theta.

13. A pharmaceutical composition comprising the solid form of claim 7 and a pharmaceutically acceptable carrier, excipient, or adjuvant.

\* \* \* \* \*